United States Patent [19]

Sagai et al.

[11] Patent Number: 5,239,065
[45] Date of Patent: Aug. 24, 1993

[54] DNA ENCODING HUMAN CV/2N SUPEROXIDE DISMUTASE MUTEINS WITH AT LEAST SERINE OR ALANINE AT EITHER OR BOTH RESIDUES 6 AND 111

[75] Inventors: Hitoshi Sagai, Mishima; Masayasu Takahara, Shizuoka; Shigeo Katsuragi, Shizuoka; Junboku Kajiwara, Shizuoka; Harumi Masujima, Mishima, all of Japan

[73] Assignee: Asahi Kasei Kogyo Kabushiki Kaisha, Osaka, Japan

[21] Appl. No.: 207,193

[22] Filed: Jun. 16, 1988

Related U.S. Application Data

[62] Division of Ser. No. 893,619, Aug. 6, 1986, Pat. No. 4,818,698.

Foreign Application Priority Data

[30]

Aug. 23, 1985 [JP] Japan .................. 60-185246

[51] Int. Cl.[5] ............................. C12N 15/53
[52] U.S. Cl. .................. 536/23.2; 435/189
[58] Field of Search ........... 435/189, 320, 691, 252.33, 435/256; 536/27

[56] References Cited

U.S. PATENT DOCUMENTS 4,518,584  5/1985  Mark et al. ................... 424/85.2
4,588,585  5/1986  Mark et al. ................... 424/85.2

OTHER PUBLICATIONS

Sherman et al. (1983) Proc. Natl. Acad. Sci., vol. 80, pp. 5465-5469.
Briggs et al. (1979) Chem. Abstr., vol. 90, No. 50326q (Abstract of Biochim. Biophys. Acta, vol. 537, pp. 86-99 (1978)).

*Primary Examiner*—Richard A. Schwartz
*Assistant Examiner*—Robert Hodges

*Attorney, Agent, or Firm*—Oblon, Spivak, McClelland, Maier & Neustadt

[57] ABSTRACT

A polypeptide represented by the following general formula (I):

| $X_1$ | Ala | Thr | Lys | Ala | Val | $X_2$ | Val | Leu | Lys | (I) |
|---|---|---|---|---|---|---|---|---|---|---|
| Gly | Asp | Gly | Pro | Val | Gln | Gly | Ile | Ile | Asn | |
| Phe | Glu | Gln | Lys | Glu | Ser | Asn | Gly | Pro | Val | |
| Lys | Val | Trp | Gly | Ser | Ile | Lys | Gly | Leu | Thr | |
| Glu | Gly | Leu | His | Gly | Phe | His | Val | His | Glu | |
| Phe | Gly | Asp | Asn | Thr | Ala | Gly | Cys | Thr | Ser | |
| Ala | Gly | Pro | His | Phe | Asn | Pro | Leu | Ser | Arg | |
| Lys | His | Gly | Gly | Pro | Lys | Asp | Glu | Glu | Arg | |
| His | Val | Gly | Asp | Leu | Gly | Asn | Val | Thr | Ala | |
| Asp | Lys | Asp | Gly | Val | Ala | Asp | Val | Ser | Ile | |
| Glu | Asp | Ser | Val | Ile | Ser | Leu | Ser | Gly | Asp | |
| His | $X_3$ | Ile | Ile | Gly | Arg | Thr | Leu | Val | Val | |
| His | Glu | Lys | Ala | Asp | Asp | Leu | Gly | Lys | Gly | |
| Gly | Asn | Glu | Glu | Ser | Thr | Lys | Thr | Gly | Asn | |
| Ala | Gly | Ser | Arg | Leu | Ala | Cys | Gly | Val | Ile | |
| Gly | Ile | Ala | Gln | | | | | | | | wherein $X_1$ means a hydrogen atom, acetyl group of amino acid residue, $X_2$ and $X_3$ are either the same or different and mean individually an amino acid residue, and when $X_2$ stands for Cys, $X_3$ denotes an amino acid residue other than Cys.

2 Claims, 8 Drawing Sheets

```
              10         20         30         40         50         60
       ATGGCGACGAAGGCCGTGTGCGTGCTGAAGGGCGACGGCCCAGTGCAGGGCATCATCAAT
       MetAlaThrLysAlaValCysValLeuLysGlyAspGlyProValGlnGlyIleIleAsn 70         80         90        100        110        120
       TTCGAGCAGAAGGAAAGTAATGGACCAGTGAAGGTGTGGGGAAGCATTAAAGGACTGACT
       PheGluGlnLysGluSerAsnGlyProValLysValTrpGlySerIleLysGlyLeuThr 130        140        150        160        170        180
       GAAGGCCTGCATGGATTCCATGTTCATGAGTTTGGAGATAATACAGCAGGCTGTACCAGT
       GluGlyLeuHisGlyPheHisValHisGluPheGlyAspAsnThrAlaGlyCysThrSer 190        200        210        220        230        240
       GCAGGTCCTCACTTTAATCCTCTATCCAGAAAACACGGTGGGCCAAAGGATGAAGAGAGG
       AlaGlyProHisPheAsnProLeuSerArgLysHisGlyGlyProLysAspGluGluArg 250        260        270        280        290        300
       CATGTTGGAGACTTGGGCAATGTGACTGCTGACAAAGATGGTGTGGCCGATGTGTCTATT
       HisValGlyAspLeuGlyAsnValThrAlaAspLysAspGlyValAlaAspValSerIle 310        320        330        340        350        360
       GAAGATTCTGTGATCTCACTCTCAGGAGACCATTCCATCATTGGCCGCACACTGGTGGTC
       GluAspSerValIleSerLeuSerGlyAspHisSerIleIleGlyArgThrLeuValVal 370        380        390        400        410        420
       CATGAAAAAGCAGATGACTTGGGCAAAGGTGGAAATGAAGAAAGTACAAAGACAGGAAAC
       HisGluLysAlaAspAspLeuGlyLysGlyGlyAsnGluGluSerThrLysThrGlyAsn 430        440        450        460
       GCTGGAAGTCGTTTGGCTTGTGGTGTAATTGGGATCGCCCAATAA
       AlaGlySerArgLeuAlaCysGlyValIleGlyIleAlaGln***
```

FIG.1

```
          10        20        30        40        50        60
ATGGCGACGAAGGCCGTGTGCGTGCTGAAGGGCGACGGCCCAGTGCAGGGCATCATCAAT
MetAlaThrLysAlaValCysValLeuLysGlyAspGlyProValGlnGlyIleIleAsn 70        80        90       100       110       120
TTCGAGCAGAAGGAAAGTAATGGACCAGTGAAGGTGTGGGGAAGCATTAAAGGACTGACT
PheGluGlnLysGluSerAsnGlyProValLysValTrpGlySerIleLysGlyLeuThr 130       140       150       160       170       180
GAAGGCCTGCATGGATTCCATGTTCATGAGTTTGGAGATAATACAGCAGGCTGTACCAGT
GluGlyLeuHisGlyPheHisValHisGluPheGlyAspAsnThrAlaGlyCysThrSer 190       200       210       220       230       240
GCAGGTCCTCACTTTAATCCTCTATCCAGAAAACACGGTGGGCCAAAGGATGAAGAGAGG
AlaGlyProHisPheAsnProLeuSerArgLysHisGlyGlyProLysAspGluGluArg 250       260       270       280       290       300
CATGTTGGAGACTTGGGCAATGTGACTGCTGACAAAGATGGTGTGGCCGATGTGTCTATT
HisValGlyAspLeuGlyAsnValThrAlaAspLysAspGlyValAlaAspValSerIle 310       320       330       340       350       360
GAAGATTCTGTGATCTCACTCTCAGGAGACCATTCCATCATTGGCCGCACACTGGTGGTC
GluAspSerValIleSerLeuSerGlyAspHisSerIleIleGlyArgThrLeuValVal 370       380       390       400       410       420
CATGAAAAAGCAGATGACTTGGGCAAAGGTGGAAATGAAGAAAGTACAAAGACAGGAAAC
HisGluLysAlaAspAspLeuGlyLysGlyGlyAsnGluGluSerThrLysThrGlyAsn 430       440       450       460
GCTGGAAGTCGTTTGGCTTGTGGTGTAATTGGGATCGCCCAATAA
AlaGlySerArgLeuAlaCysGlyValIleGlyIleAlaGln***
```

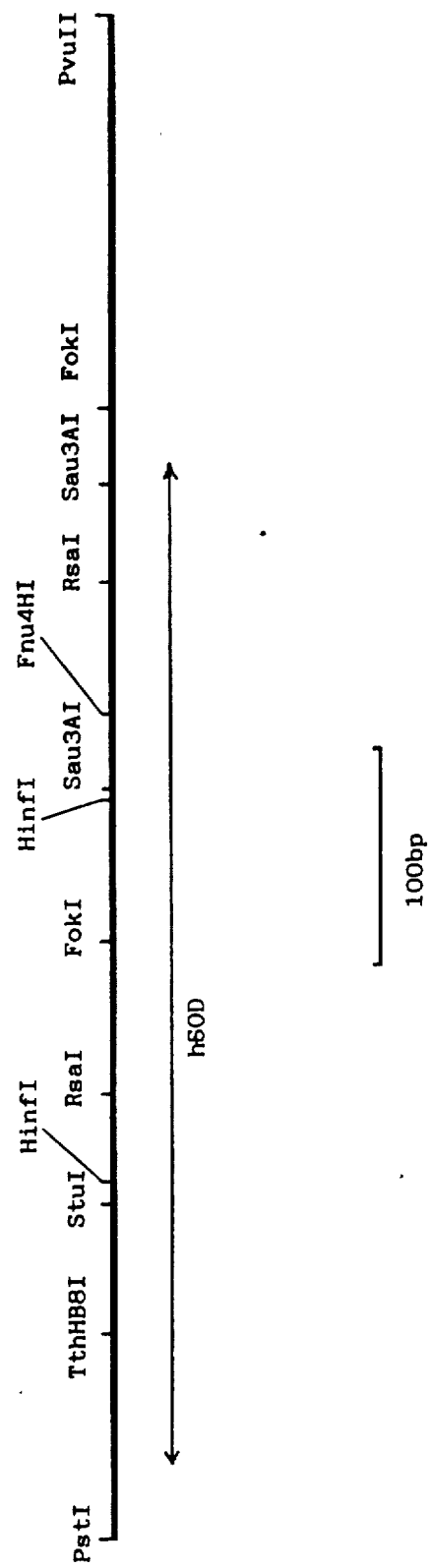

FIG. 3

```
                                GGGGGGGGGGGGGGGGGGGGGGGCCTAGCGAGTT
         10        20        30        40        50        60
ATGGCGACGAAGGCCGTGTGCGTGCTGAAGGGCGACGGCCCAGTGCAGGGCATCATCAAT
MetAlaThrLysAlaValCysValLeuLysGlyAspGlyProValGlnGlyIleIleAsn 70        80        90       100       110       120
TTCGAGCAGAAGGAAAGTAATGGACCAGTGAAGGTGTGGGGAAGCATTAAAGGACTGACT
PheGluGlnLysGluSerAsnGlyProValLysValTrpGlySerIleLysGlyLeuThr 130       140       150       160       170       180
GAAGGCCTGCATGGATTCCATGTTCATGAGTTTGGAGATAATACAGCAGGCTGTACCAGT
GluGlyLeuHisGlyPheHisValHisGluPheGlyAspAsnThrAlaGlyCysThrSer 190       200       210       220       230       240
GCAGGTCCTCACTTTAATCCTCTATCCAGAAAACACGGTGGGCCAAAGGATGAAGAGAGG
AlaGlyProHisPheAsnProLeuSerArgLysHisGlyGlyProLysAspGluGluArg 250       260       270       280       290       300
CATGTTGGAGACTTGGGCAATGTGACTGCTGACAAAGATGGTGTGGCCGATGTGTCTATT
HisValGlyAspLeuGlyAsnValThrAlaAspLysAspGlyValAlaAspValSerIle 310       320       330       340       350       360
GAAGATTCTGTGATCTCACTCTCAGGAGACCATTGCATCATTGGCCGCACACTGGTGGTC
GluAspSerValIleSerLeuSerGlyAspHisCysIleIleGlyArgThrLeuValVal 370       380       390       400       410       420
CATGAAAAAGCAGATGACTTGGGCAAAGGTGGAAATGAAGAAAGTACAAAGACAGGAAAC
HisGluLysAlaAspAspLeuGlyLysGlyGlyAsnGluGluSerThrLysThrGlyAsn 430       440       450       460
GCTGGAAGTCGTTTGGCTTGTGGTGTAATTGGGATCGCCCAATAAACATTCCCTTGGATG
AlaGlySerArgLeuAlaCysGlyValIleGlyIleAlaGln***

TAGTCTGAGGCCCCTTAACTCATCTGTTATCCTGCTAGCTGTAGAAATGTATCCTGATAA

ACATTAAACACTGTAATCTTAAAAAAAAAAA
``` synthetic DNA

5'AATTCTGATAAGGAGGTCAAAAAAATGGCGACGAAGGCCGTGTGCGTGCT
3'GACTATTCCTCCAGTTTTTTTACCGCTGCTTCCGGCACACGCACGA

GAAGGGCGACGGCCCAGTGCAGGGCATCATCAATTT3'
CTTCCCGCTGCCGGGTCACGTCCCGTAGTAGTTAAAGC5'

DNA ENCODING HUMAN CV/2N SUPEROXIDE DISMUTASE MUTEINS WITH AT LEAST SERINE OR ALANINE AT EITHER OR BOTH RESIDUES 6 AND 111

This is a division of application Ser. No. 06/893,619, filed Aug. 6, 1986 now U.S. Pat. No. 4,818,698.

BACKGROUND OF THE INVENTION

1. Field of the Invention

This invention relates to polypeptides analogous to human superoxide dismutase, which have a sequence of at least 153 amino acids and represented by the following general formula (I):

| $X_1$ | Ala | Thr | Lys | Ala | Val | $X_2$ | Val | Leu | Lys | (I) |
| 10 | | | | | | | | | | |
| Gly | Asp | Gly | Pro | Val | Gln | Gly | Ile | Ile | Asn | |
| 20 | | | | | | | | | | |
| Phe | Glu | Gln | Lys | Glu | Ser | Asn | Gly | Pro | Val | |
| 30 | | | | | | | | | | |
| Lys | Val | Trp | Gly | Ser | Ile | Lys | Gly | Leu | Thr | |
| 40 | | | | | | | | | | |
| Glu | Gly | Leu | His | Gly | Phe | His | Val | His | Glu | |
| 50 | | | | | | | | | | |
| Phe | Gly | Asp | Asn | Thr | Ala | Gly | Cys | Thr | Ser | |
| 60 | | | | | | | | | | |
| Ala | Gly | Pro | His | Phe | Asn | Pro | Leu | Ser | Arg | |
| 70 | | | | | | | | | | |
| Lys | His | Gly | Gly | Pro | Lys | Asp | Glu | Glu | Arg | |
| 80 | | | | | | | | | | |
| His | Val | Gly | Asp | Leu | Gly | Asn | Val | Thr | Ala | |
| 90 | | | | | | | | | | |
| Asp | Lys | Asp | Gly | Val | Ala | Asp | Val | Ser | Ile | |
| 100 | | | | | | | | | | |
| Glu | Asp | Ser | Val | Ile | Ser | Leu | Ser | Gly | Asp | |
| 110 | | | | | | | | | | |
| His | $X_3$ | Ile | Ile | Gly | Arg | Thr | Leu | Val | Val | |
| 120 | | | | | | | | | | |
| His | Glu | Lys | Ala | Asp | Asp | Leu | Gly | Lys | Gly | |
| 130 | | | | | | | | | | |
| Gly | Asn | Glu | Glu | Ser | Thr | Lys | Thr | Gly | Asn | |
| 140 | | | | | | | | | | |
| Ala | Gly | Ser | Arg | Leu | Ala | Cys | Gly | Val | Ile | |
| 150 | | | 153 | | | | | | | |
| Gly | Ile | Ala | Gln | | | | | | | | wherein $X_1$ means a hydrogen atom, acetyl group or amino acid residue, $X_2$ and $X_3$ are either the same or different and mean individually an amino acid residue, and when $X_2$ stands for Cys, $X_3$ denotes an amino acid residue other than Cys, and their preparation process, as well as their copper- and/or zinc-coordinated dimers represented by the following formula (II):

$$2\,[\text{polypeptide (I)}].Y_1 Cu^{2+}.Y_2 Zn^{2+} \qquad (II)$$

wherein $Y_1$ and $Y_2$ stand individually for an integer of 0–4 and $Y_1 + Y_2$ is 2 or 4.

2. Description of the Prior Art

Superoxide dismutase (hereinafter abbreviated as "SOD") is a compound which was found for the first time by Fridovich, McCord, et al. J. Biol. Chem. 244, No. 22, 6049–6063 (1969) as an enzyme capable of converting superoxides, intermediates in oxidations by xanthine oxidase, in the course of their investigation on xanthine oxidase. It can be purified by a variety of methods, for example, heat treatment [Japanese Patent Publication Nos. 39832/1970 and 48721/1974; Sugiura, et al., J. Pharm. Dyn. 4, 235–244 (1981); etc.], salting-out with ammonium sulfate and precipitation in an organic solvent [Japanese Patent Laid-Open No. 155991/1982; Stephen, A. G, et al., Biochimica et Biophysica Acta, 289, 276–283 (1972)], gel filtration chromatography (Japanese Patent Laid-Open Nos. 102787/1981 and 10382/1982), affinity chromatography (Japanese Patent Laid-Open No. 121791/1983), etc. This SOD has drawn attention from the viewpoint of the oxygen toxicity protective mechanism in living bodies. It is now used as an anti-inflammatory for the treatment of chronic arthrorheumatic osteoarthritis, radiation-induced side effects, certain urosis and the like. Especially, bovine liver SOD is used clinically.

In the meantime, the sequence of amino acids in human erythrocyte Cu—Zn—SOD has been reported recently [Jabusch, et al., Biochemistry, 19, 2310–2316 (1980); and Barra, et al., FEBS Letters, 120, 53–55 (1980)]. There is also a report on the sequence of bases in a gene of human-origin SOD (hereinafter called "h-SOD") [Sherman, et al., Proc. Natl. Acad. Sci. U.S.A., 80, 5465–5469 (1983)]. Production of h-SOD in Escherichia coli (hereinafter called "E. coli) and yeast by a genetic operation has also been reported (Japanese Patent Laid-Open No. 137286/1985).

In order to use SOD clinically especially as an anti-inflammatory or for other therapeutic purposes, it is essential that physiologically-acceptable SOD is supplied stably. To permit in vivo application of SOD in human bodies, SOD is required, in view of predictable immunological problems, to be h-SOD or at least an h-SOD analogous polypeptide in an immunologically acceptable class and also to be a homogeneous enzyme. However, h-SOD has had a problem in its stable supply.

SUMMARY OF THE INVENTION

With a foregoing in view, the present invention has as its object the provision of novel h-SOD analogous polypeptides useful as medicines. As a result, it has been found that recombinant h-SOD can be advantageously obtained when a genetic operation is used.

The recombinant h-SOD (I) has activities equal to or higher than native h-SOD. Unlike native h-SOD, charged isomers are not observed therein. It is therefore a high-purity product having extremely high stability. Compared with native h-SOD, it is also extremely stable along the passage of time in aqueous solutions or water-organic solvent solutions. In addition, it is free from side effects such as antigenicity. The recombinant h-SOD (I) of this invention can therefore be used effectively, e.g., as anti-inflammatory and medicines for other therapeutic purposes, as raw materials for clinical diagnoses, etc.

The above and other objects, features and advantages of the present invention will become apparent from the following description and the appended claims, taken in conjunction with the accompanying drawings.

BRIEF DESCRIPTION OF THE DRAWINGS

FIG. 1 illustrates the base sequence of the SOD polypeptide of a plasmid pSOD14 constructed in Example 1;

FIG. 2 shows the restriction endonuclease map of a DNA fragment containing the h-SOD gene;

FIG. 3 depicts the h-SOD gene and its corresponding polypeptide composed of 153 amino acids;

DETAILED DESCRIPTION OF THE INVENTION AND PREFERRED EMBODIMENTS

Figure 4:
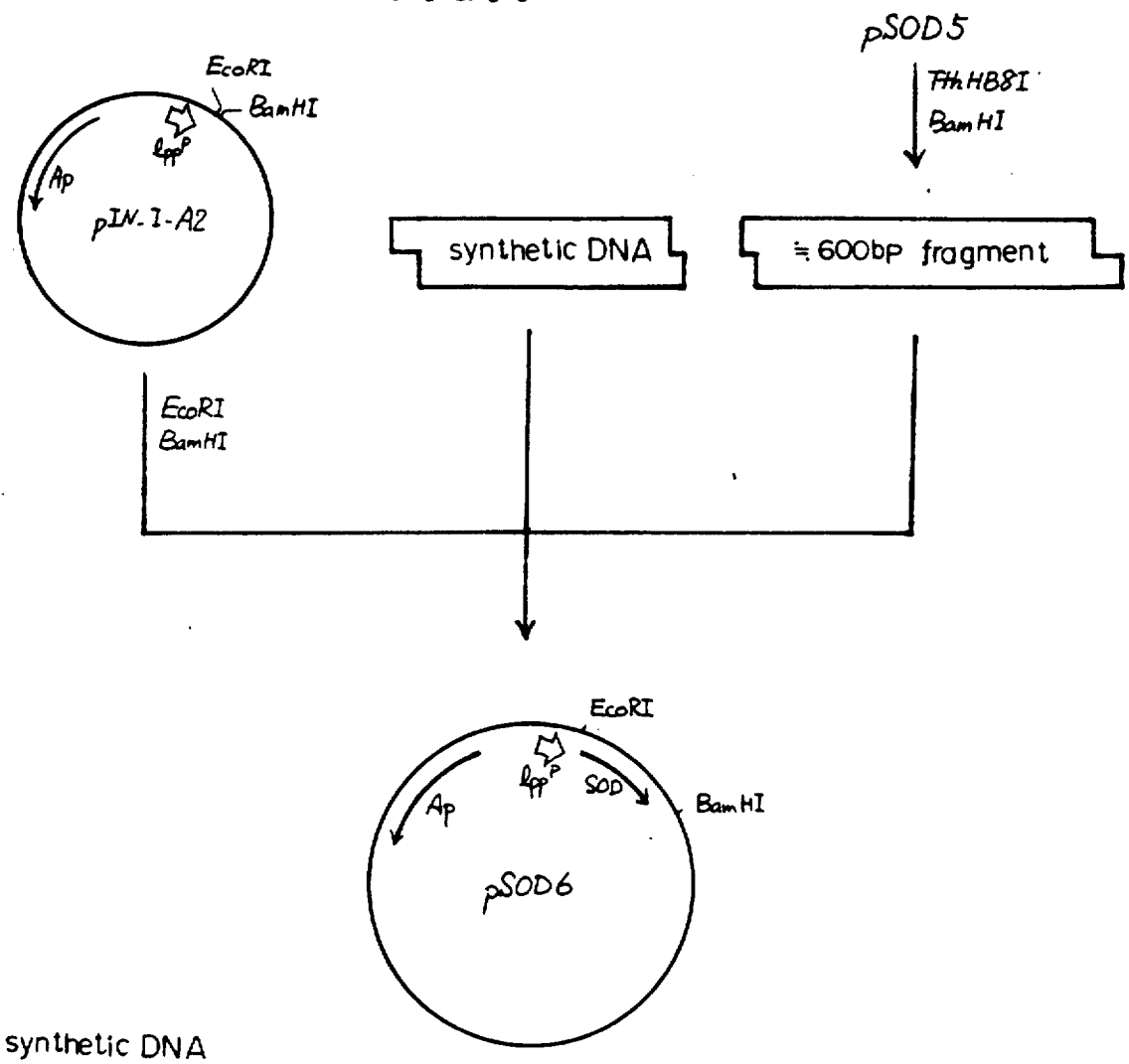
FIG. 4 is a simplified flow chart of recombination for the construction of a plasmid pSOD6.

With a final target on h-SOD, the present inventors first of all collected RNA from the tissue of a normal human liver which had been enucleated. After obtaining poly(A)+RNA, c-DNA was synthesized in accordance with the routine procedure in genetic engineering. Subsequent to its recombination into a vector, E. coli was then transformed by using the vector The E. coli was thereafter cultured, followed by screening of a clone having the h-SOD gene from the resultant colony. From the above clone, DNA having the h-SOD gene was obtained by using as a probe a synthetic nucleotide corresponding to the 5-amino acid moiety, $-5'ATGGCGACGAAGGCC3'-$ of the N-terminal of h-SOD. By restriction endonucleases Pst I and Pvu II, the gene was obtained as a 700 bp DNA fragment containing the h-SOD gene. Furthermore, a restriction enzyme map illustrated in FIG. 2 was obtained from the above DNA fragment by using restriction endonucleases TthHB8I, Stu I, Hinf I, Rsa I, Fok I, Fnu 4HI and Sau 3AI. Based on the restriction enzyme map, the base sequence in the code region of the h-SOD polypeptide was provided by the Maxam-Gilbert method [Method Enzymol, 65, 449 (1979)], thereby determining the polypeptide sequence of h-SOD and the base sequence coding the polypeptide sequence as illustrated in FIG. 3. The present inventors proceeded with a further research on the base sequence coding the sequence of the amino acids in the h-SOD polypeptide with a view toward converting the Cys at the 111-site and/or 6-site (as counted from the Ala of the polypeptide) into other amino acid residues in accordance with a site-specific mutagenesis method. As a result, a base sequence capable of achieving this object was obtained It has then been found that recombinant polypeptides represented by the above formula (I) and having h-SOD activity (hereinafter called "recombinant h-SODs") and copper- and/or zinc-coordinated recombinant h-SOD dimers represented by the above formula (II) can be obtained by using the base sequence and E. coli in accordance with the routine procedure in genetic engineering. It has also been uncovered that the dimers (II) of the recombinant h-SODs (I) are obtained as homogeneous enzymes and are stable h-SOD-like polypeptides having activities equal to or higher than h-SOD.

The present invention has been completed on the basis of these findings.

Among the recombinant h-SODs (I) of this invention, may be mentioned as preferred examples those represented by the general formula (I) in which $X_2$ is a neutral amino acid residue, e.g., Cys, Ser, Ala or Thr and $X_3$ is a neutral amino acid residue, e.g., Ser, Ala or Thr. Of these, particularly preferred are polypeptides of the general formula (I) in which $X_1$ is a hydrogen atom or an acetyl group, $X_2$ means Cys and $X_3$ denotes. Ser. Among the recombinant h-SOD dimers (II), may be mentioned as preferred examples those represented by the general formula (II) in which $Y_1$ and $Y_2$ are both 2 and $Y_1$ and $Y_2$ are 4 and 0 respectively.

Polymers formed of these dimers (II) as their constituent units and having SOD activities are also included in the present invention.

For the preparation of each of the h-SODs (I) and their dimers (II) of this invention, a recombinant DNA is constructed from a polydeoxyribonucleic acid having a base sequence coding the amino acid sequence of polypeptide of the formula (I) and a replicative vector. A bacterial host is transformed using the recombinant DNA. The transformant is then cultured in a culture medium to produce the desired polypeptide gene, followed by collection of the desired product from the cultured cell broth.

In order to construct the recombinant DNA of the polydeoxyribonucleic acid, which has the base sequence coding the recombinant h-SOD (I), and the replicative vector, it is only necessary to insert the polydeoxyribonucleric acid coding the recombinant h-SOD (I) into a known replicative vector from the known DNA libraries described in the known literature referred to supra [Proc. Natl. Acad Sci. U.S.A., 80, 5465–5469 (1983); Japanese Patent Laid-Open No. 137286/1985] by a technique known in genetic engineering.

As to the technique known in genetic engineering, the above insertion may be practised in accordance with a number of literature on genetic engineering, for examples, manuals of experiments such as:

(1) TAKAGI, Yasuyuki, "Idenshi Sosa Manual (Manual of Genetic Operations)", Kodansha;
(2) TAKAGI, Yasuyuki, "Idenshi Sosa Jikkenho (Laboratory Manual of Genetic Operations), Kodansha;
(3) MANIATIS, T., et al., "Molecular Cloning: "Laboratory Manual", Cold Spring Harber Laboratory, Cold. Sp. Harb., U.S.A.; and
(4) WU, Ray, et. al., "Method in Enzymology", 101, Academic Press, U.S.A.

For example, it is only necessary to obtain the liver cDNA library from a human liver by molecular cloning with respect to h-SOD cDNA, to transform a bacterial host by the liver cDNA library, to conduct clone screening on the resultant transformant by the colony hybridization method to obtain an h-SOD-coding plasmid, and then to integrate the h-SOD-coding region into a producing vector. The outline of this procedure is shown in FIG. 4.

By subjecting the thus-obtained recombinant DNA (pSOD6), which is used for the production of h-SOD, to a site-specific mutagenesis method, it is possible to construct a replicative recombinant DNA having a base sequence coding the sequence of the constituent amino acids of the recombinant h-SOD (I) one or two amino acids of which are different from the amino acid sequence of h-SOD.

Figure 5:
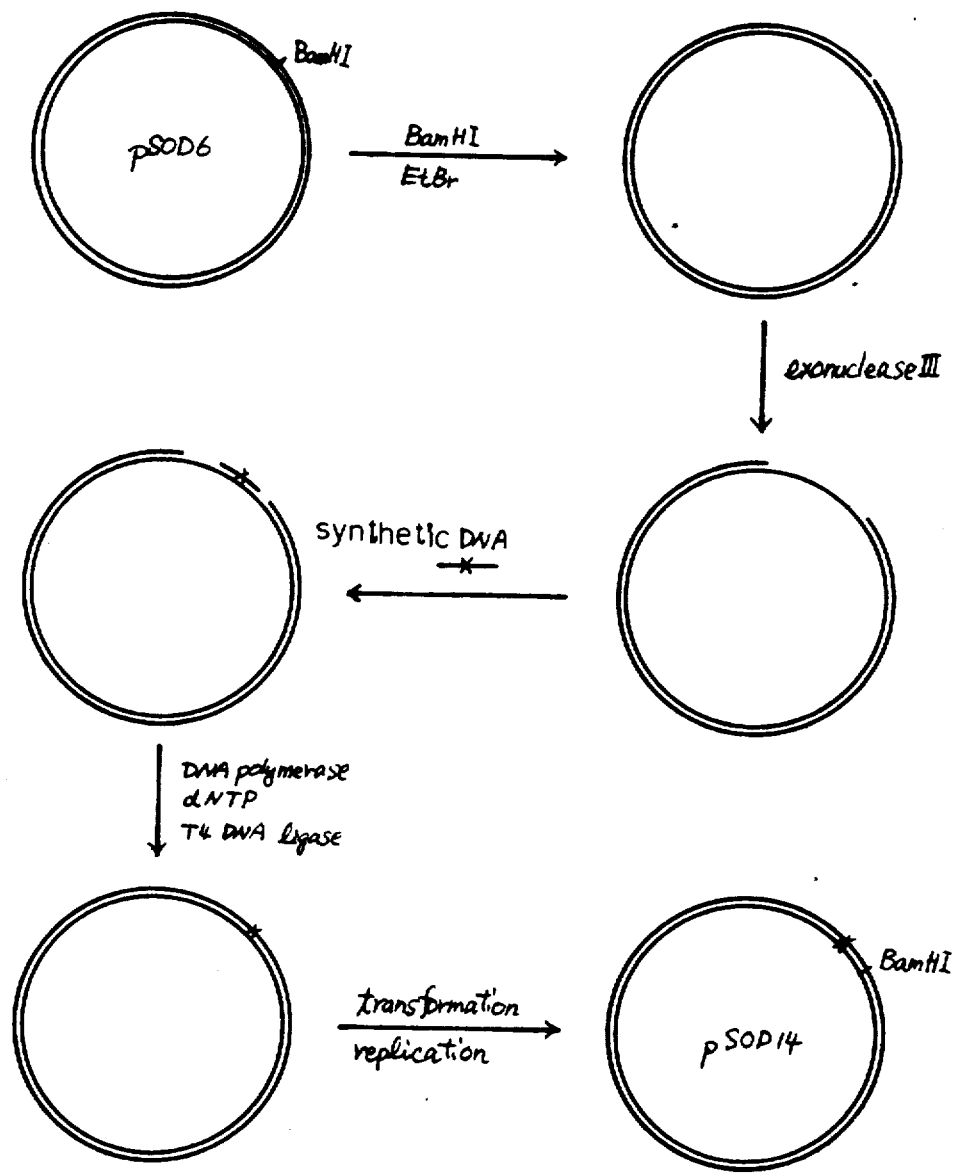
FIG. 5 is a simplified flow chart of recombination for the construction of the plasmid pSOD14.

As the above site specific mutagenesis method, the following method may be mentioned. Namely, BamHI was caused to act on pSOD6 of the closed circle structure (cc) in the presence of ethidium bromide (EtBr) under light-shielded conditions, whereby pSOD6 was converted into the open circle structure (oc). Exonuclease III was then caused to act, whereby the DNA at the site where mutagenesis was desired was converted into a single strand form. The resultant synthetic nucleotide having the mutable site was annealed to the partly single-strand plasmid. DNA polymerase and $T_4$DNA ligase were then caused to act in the presence of dNTP so that the synthetic nucleotide was incorporated in the plasmid ["Experimental Manipulation of Gene Expression", 291-303 (1983), Academic Press]. The outline of this recombination procedure is shown in FIG. 5.

In the manner described above, the plasmid pSOD14 DNA containing the h-SOD gene having for example a base code TCC in which the Cys (TGC) at the 111th site counted from Ala has been varied to Ser is obtained.

As illustrative synthetic nucleotides useful in the above-described variation method, various synthetic nucleotides given in the following Table 1 may be mentioned. By using these synthetic nucleotides, their corresponding plasmids are obtained.

TABLE 1

| Amino acid | Synthetic nucleotide (codon)* | Raw material plasmid | Constructed plasmid |
|---|---|---|---|
| Cys | GAGACCAT\|TGC\|ATCATTGG | | |
| Ser | AGACCAT\|TCC\|ATCATTG | pSOD6 | pSOD14 |
| Tyr | AGACCAT\|TAC\|ATCATTG | " | pSOD35 |
| Ala | GAGACCAT\|GCC\|ATCATT | pSOD14 | pSOD36 |
| Phe | AGACCAT\|TTC\|ATCATTG | pSOD6 | pSOD37 |
| Trp | AGACCAT\|TGG\|ATCATTG | " | pSOD38 |
| Arg | GAGACCAT\|CGC\|ATCATT | " | pSOD39 |
| Gly | GAGACCAT\|GGC\|ATCATT | " | pSOD40 |
| Pro | GAGACCAT\|CCC\|ATCATT | pSOD14 | pSOD41 |
| Thr | GAGACCAT\|ACC\|ATCATT | " | pSOD42 |
| His | GAGACCAT\|CAC\|ATCATT | pSOD35 | pSOD43 |
| Asn | GAGACCAT\|AAC\|ATCATT | " | pSOD44 |
| Asp | GAGACCAT\|GAC\|ATCATT | " | pSOD45 |
| Leu | GACCAT\|TTG\|ATCATTGG | pSOD37 | pSOD46 |
| Ile | GAGACCAT\|ATC\|ATCATT | " | pSOD47 |
| Val | GAGACCAT\|GTC\|ATCATT | " | pSOD48 |
| Gln | GACCAT\|CAA\|ATCATTGG | pSOD43 | pSOD49 |
| Lys | GACCAT\|AAA\|ATCATTGG | pSOD44 | pSOD50 |
| Glu | GACCAT\|GAA\|ATCATTGG | pSOD45 | pSOD51 |
| Met | GAGACCAT\|ATG\|ATCATT | pSOD46 | pSOD52 |

*between the dashed lines.

Other methods described in literature may also be applied besides the above-mentioned site-specific mutagenesis method [Proc. Natl. Acad. Sci. U.S.A., 81, 4008 (1984); Nucl. Acid. Res., 10, 6487 (1982)].

In order to convert, for example, the Cys at the 6-site counting from the Ala into another amino acid, it is only necessary to isolate a fragment of an h-SOD analogous gene, for example, from pSOD14, to split at an appropriate site downstream the TGC coding the 6-site Cys with a restriction endonuclease, and then to bind a synthetic nucleotide having a codon coding an amino acid other than Cys (TGC), for example, 5'-TGTCCGTGCTGAAGGG-3' having the codon TCC of Ser. Plasmid pSOD53 prepared above by way of example has a code capable of producing a recombinant h-SOD in which the Cys at each of the 6-site and 111-site of h-SOD has been replaced by Ser.

As host cells preferable for the cloning and/or replication of genes coding the recombinant h-SOD (I) of this invention, may be mentioned those capable of being grown in cultures of fermentation out of procaryotes such as bacteria and eucaryotes such as Yeast and monkey kidney cells. Particularly preferred are E. coli, Bacillus subtilis, Saccharomyces cerevisiae, Streptomyces, and COS cells originated from monkey kidney cells.

As the above vector, vectors of various kinds usable in the above-described cells may be used. They can be derived from plasmids and virus as needed. Vectors function for cloning and/or replication. There are a number of literature on vectors and numerous vectors are commercially available. These vectors generally contain markers by which their screening is feasible. There are cytotoxic resistance, auxotrophism and the like as these markers. A single vector may often contain many vectors which impart different characteristics. In the case of a cloning vector, there are both control signals of transcription start and transcription stop.

As such advantageously usable vectors, may be mentioned, for example, vectors containing 1 pp promoters such as pIN-I, pIN-II and pIN-III (PKEN vectors), vectors containing pho5 promoters such as pAM82, SV40 vectors such as plasmid pSV2, and so on.

When yeast is employed as the host organism for the expression, the DNA which is useful in the practice of this invention is not necessarily limited to pTJ102-SOD14 employed in Examples, which will be described subsequently, but any yeast vectors may also be applicable provided that they contain a promoter functional in yeast and a DNA sequence capable of being transcribed by the above-mentioned functional promoter to an m-RNA from which h-SOD or an h-SOD derived polypeptide described in this specification can be translated. The yeast vector may be either any one of the vectors in the three types [YI$_p$, YE$_p$ and YR$_p$ types] classified by Struhl, et al. [Struhl, K., Stinchcomb, D. T., Sherer, S., Davis, R. W.: Proc. Natl. Acad. Sic. U.S.A., 76,1035(1979)] or any one of the YC$_p$ type vectors classified by Clarke, et al. [Clarke, L., Carbon, J.: "Nature", 287, 504(1980)]. As a further alternative, it may be a vector which is a combination of more than one type of vectors like pAM82. As a still further alternative, the yeast vector may be a shuttle vector such as pAM82, which additionally carries a DNA sequence required for the replication and maintenance of the plasmid in E. coli.

The promoter may be chosen not only from Pho5 promoter but also from ADH1 promoter [V. M. Williamson, J. Bennetzen, E. T. Young, K. Naysmith & B. D. Hall: Nature, 283, 214(1980)], Gal10 promoter [St. John, T. P., Davis, R. W.: "Cell", 16, 443(1979)] and other known promoters. Promoter-screening methods have also been reported, for example, by Akio Tohe in "Kagaku to Seibutsu (Chemistry & Living Organism)", 21, 183-193 (1983). A DNA with a promoter sequence may hence be obtained, for example, by following the screening method introduced by him.

In addition, it should also be noted that the yeast strain useful in the practice is not necessarily limited to AH22 strain. Any strains which belong to Saccharomy-

*ces corevisiae* may basically be used. If a none-YI$_p$ type vector is used, it is however necessary to introduce it into a host strain which has an auxotrophic mutation like leu$^{2-}$ mutation in AH22 strain. Accordingly, the vector is supposed to have a DNA sequence capable of complementing the above mutation. This is one of routine techniques practiced for the stable maintenance of plasmids on their corresponding host cells. Yeasts other than *S. cerevisiae* may also be employed to achieve expression of h-SOD and the h-SOD derivatives described in the present specification, provided that yeast vectors appropriate to such other yeasts are used.

As a culture medium useful in obtaining the recombinant h-SOD (I) from the resultant transformant, known culture media employed for this purpose may be mentioned. Preferred are culture media containing suitable amounts of copper and/or zinc ions therein.

The recombinant h-SOD (I) of this invention can be obtained by culturing the transformant at 30°–42° C., preferably around 37° C., for 3–48 hours by a known method, for example, the aerated stirring culturing method, shaking culturing method, rotation culturing method, standstill culturing method or the like. Where the recombinant h-SOD (I) is replicated within cells, the cells are separated by centrifugation when the cultured cell broth has reached a high concentration. The cells are lysed, followed by separation and purification of the recombinant h-SOD (I) by the various methods described in the above-described literature, for example, extraction, ion exchange chromatography, affinity chromatography, electrophoresis or dialysis or a combination thereof. Where the product is secreted, the culture medium is processed in a similar manner.

According to the above-described process of this invention, the recombinant h-SOD (I) is obtain first of all as a copper- and/or zinc-coordinated dimer represented by the formula (II). The recombinant h-SOD (I) can however be obtained with ease provided that the dimer is treated in a manner known per se in the art.

Having generally described the invention, a more complete understanding can be obtained by reference to certain specific examples, which are provided herein for purpose of illustration only and are not intended to be limiting unless otherwise specified.

EXAMPLES

The present invention will hereinafter be described by the following Referential Examples and Examples. It should however be born in mind that this invention is not necessarily limited to or by them.

REFERENTIAL EXAMPLE 1

Preparation of h-SOD poly(A)+RNA (i) After homogenizing 5 g of normal human liver tissue in 25 ml of 4M guanidine isothiocyanate, the homogenate was maintained at 60° C. Phenol in the same volume was then added and mixed. The mixture was passed through an 18-gauge injection needle, 10 times, so that the DNA was split and the viscosity was reduced, followed by addition of 12.5 ml of a liquid mixture consisting of 0.1M sodium acetate, 10 mM Tris-HCl (pH 7.4) and 1 mM EDTA and 25 ml of chloroform-isoamyl alcohol (24:1). The resultant mixture was stirred at 60° C. for 10 minutes, cooled in ice and then centrifuged at 10,000 rpm for 10 minutes, thereby obtaining a water layer. The same volume of chloroform-phenol was added to the water layer. The resultant mixture was stirred at 60° C. for 10 minutes and then cooled in ice. By centrifugation at 10,000 rpm for 10 minutes, a water layer was obtained. After extraction for removal of the phenol twice with the same volume of chloroform-isoamyl alcohol, 2 volumes of ethanol were added and the resultant mixture was allowed to stand at −20° C. for 2 hours. The precipitate was collected by centrifugation at 10,000 rpm for 30 minutes, dissolved with 25 ml of a solution containing 0.1M Tris-HCl (pH 7.4), 50 mM NaCl, 10 mM EDTA, 0.2% SDS (sodium dodecylsulfate) and 5 mg "Proteinase K" (protease; product of Merck & Co., Inc.), incubated at 37° C. for 1.5 hours. The temperature was raised to 60° C., followed by addition of 12.5 ml of phenol and 12.5 ml of chloroformisoamyl alcohol. After stirring the resultant mixture at 60° C. for 10 minutes, it was cooled in ice and centrifuged at 10,000 rpm for 10 minutes to obtain a water layer. The water layer was treated again with phenol, followed by extraction of the chloroform twice. After an addition of 2 volumes of ethanol, the resultant mixture was centrifuged and the precipitate was collected and was then dried under reduced pressure. In the above manner, 4.04 mg of crude RNA was obtained.

(ii) After dissolving the above-obtained precipitate in 5 ml of sterilized water, the solution was incubated at 65° C. for 5 minutes and then chilled quickly, followed by addition of 5 ml of a solution containing 40 mM Tris-HCl (pH 7.6), 1.0M NaCl, 2 mM EDTA and 0.2% SDS. The entire volume of the resultant mixture was caused to pass for adsorption through a column packed with 0.2 g oligo(dT)-cellulose (product of Colaborative Company) which had been equilibrated by a mixture of 20 mM Tris-HCl (pH 7.6), 0.5M NaCl, 1 mM EDTA and 0.2% SDS. After washing the column with 10 ml of the same solution, RNAs other than poly(A)+RNA were eluted first of all with an eluant consisting of 5 ml of 20 mM Tris-HCl (pH 7.6), 0.1M NaCl, 1 mM EDTA and 0.1% SDS. Then, poly(A)+RNA was eluted with an eluant consisting of 10 mM Tris-HCl (pH 7.5), 1 mM EDTA and 0.05% SDS. The eluate was fractionated 1 ml by 1 ml. By measuring the OD$_{260}$ value, Fraction No. 2 - Fraction No. 8 were collected as poly(A)+RNA fractions. To those fractions, 1/10 volume of 2.5M sodium acetate and 2 volumes of ethanol were added. After allowing the resultant mixture to stand overnight at −20° C., it was centrifuged at 25,000 rpm for 20 minutes to obtain a precipitate and the precipitate was then dried under reduced pressure. In this manner, 14.4 μg of poly(A)+RNA was obtained.

REFERENTIAL EXAMPLE 2

Synthesis and cloning of cDNA (i) The synthesis and cloning of cDNA were conducted in accordance with the Okayama-Berg method [Mol. Cell. Biol. 2, 161 (1982)]. The poly(A)+RNA (114.4 μg) obtained in Referential Example 1 was dissolved in 100 μl water. A 4 μl aliquot of the resultant solution was transferred in a microtube and then dried under reduced pressure. It was then dissolved with 10 μl of 5 mM Tris-HCl (pH 8.3) and heated at 65° C. for 5 minutes. After lowering its temperature to 37° C., 20 μl of a solution containing 50 mM Tris-HCl (pH 8.3), 8 mM MgCl$_2$, 30 mM KCl, 0.3 mM dithiothreitol and 2 mM dNTP (a mixture of dATP, dGTP, dCTP and dTTP in the same amounts), 10 μCi 1.4 μg vector primer DNA (product of PL-Biochemical Company), and 5 units reverse transcriptase (product of Life Science Company) were added and then reacted at 37° C. for 20 minutes. The reaction mixture was thereafter added with 2 μl of 0.25M EDTA and 1 μl of 10% SDS to terminate the reaction, followed by a treatment with 20 μl phenol-chloroform. To a water layer which had been obtained by centrifugation, the same volume of 4M ammonium acetate and 80 μl of ethanol were added and the resultant mixture was left over at −70° C. for 15 minutes. A precipitate obtained by centrifugation at 15,000 rpm for 10 minutes was dissolved in 10 μl of a mixed solution (may hereinafter be abbreviated as "TE") of 10 mM Tris-HCl (pH 8.0) and 1 mM EDTA. The ethanol precipitation was repeated again, and after washing once with 50 μl of 75% ethanol, the precipitate was dried under reduced pressure. It was then dissolved with 15 μl of a solution containing 140 mM sodium cacodylate, 30 mM Tris-HCl (pH 6.8), 1 mM $CoCl_2$, 0.1 mM dithiothreitol, 0.2 μg of "Poly A" (product of Sigma Company) and 10 μCi[α-$^{32}$P]dCTP. While incubating the resultant solution at 37° C., 18 units of a terminal transferase (product of PL-Biochemical Company) were added. They were reacted at 37° C. for 20 minutes, phenol-chloroform treated, ethanol precipitated, ethanol washed, dried and then dried under reduced pressure. The thus-obtained product was dissolved with 10 μl of a solution containing 50 mM NaCl, 10 mM Tris-HCl (pH 7.4), 10 mM $MgCl_2$ and 1 mM dithiothreitol, added with 2.5 units of "Hind III" (product of Takara Shuzo Co., Ltd.), and incubated at 37° C. for 1 hour. After chloroform-phenol treatment, ethanol precipitation, ethanol washing and drying, the resultant precipitate was redissolved in 10 μl of TE, added with 3 μl of ethanol and then stored at 20° C. A solution which had been prepared by dissolving 7 ng of an oligo(dG)integrated linker DNA (product of PL-Biochemical Company) with 10 μl TE (pH 7.5) containing 0.1M NaCl was added to a 1 μl aliquot of the above-obtained solution. The resultant solution was incubated at 65° C. for 5 minutes and at 42° C. for further 30 minutes and was then chilled to 0° C. Thereafter, the solution was brought to contain 20 mM Tris-HCl (pH 7.5), 4 mM $MgCl_2$, 10 mM $(NH_4)_2SO_4$, 0.1M KCl, 0.1 mM β-AND, 50 μg/ml BSA, and 0.6 μg E. coli DNA ligase (product of PL-Biochemical Company) and water was added to bring the total volume to 100 μl. The resultant mixture was then left over overnight at 12° C. After adding 1 μl of 4 mM dNTP, 1 μl of 15 mM β-AND, 1 μl of E. coli DNA ligase (0.4 μg; product of PL-Biochemical Company), 1 μl of DNA polymerase I (0.3 μg; product of PL-Biochemical Company), 1 μl of E. coli RNaseH (1 unit; product of PL-Biochemical Company), the resultant mixture was incubated at 12° C. for 1 hour and at 25° C. for further 1 hour.

(ii) E. coli DH1 [J. Mol. Biol., 166, 557(1983); an E. coli strain supplied courteously from the Genetic Stock Center, School of Medicine, Yale University (Stock No. CGSC Strain 6040)], which had been cultured in 100 ml BHI culture medium (product of DIFCO Company; a bovine brain-heart extract medium) and was in the logarithmic phase of growth, was harvested and then suspended in 40 ml of an ice-chilled solution (pH 5.8) of 30 mM potassium acetate, 100 mM RbCl, 10 mM $CaCl_2$, 50 mM $MnCl_2$ and 15% glycerin. After allowing the suspension to stand at 0° C. for 5 minutes, the cells were collected by centrifugation, followed by their suspension in a solution (pH 6.5) of 4 ml of 10 mM MOPS buffer (product of Dotai Company), 75 mM $CaCl_2$, 10 mM RbCl and 15% glycerin. The suspension was left over at 0° C. for 15 minutes to obtain competent cells.

(iii) A 20 μl aliquot of the DNA solution prepared in (i) was added to 200 μl of the E. coli suspension and the resultant mixture was allowed to stand at 0° C. for 30 minutes. The mixture was heat-treated at 42° C. for 90 seconds, to which 800 μl of the LB (Luria-Bertani) culture medium (10 g bactotrypton, 5 g bactoyeast extract, 10 g NaCl, 1 l water; pH 7.5), followed by incubation at 37° C. for 90 minutes. Its 100 μl aliquot was spread on an LB agar plate containing 50 μg/ml ampicillin and was cultured overnight to obtain a transformant.

REFERENTIAL EXAMPLE 3

Screening of h-SOD clone

The screening of the h-SOD gene clone was conducted on the transformant, which had been obtained after the overnight culturing, by using the colony hybridization method. After transferring onto a nitrocellulose membranes the colonies grown on the LB agar, the membranes were placed on LB agar media containing chloramphenicol (100 μg/ml) with the colony-bearing side up. The membranes were incubated overnight at 37° C. to amplify the plasmids DNA in the cells. After treatment of the membranes for 5 minutes in 0.5N NaOH, for 3 minutes in 1M Tris-HCl (pH 7.4) and for further 5 minutes in 0.5M Tris-HCl (pH 7.5)-1.5M NaCl, the membranes were dried at 80° C. for 3 hours. Then, the membranes were enclosed in a polyvinyl chloride bag and was subjected to a washing treatment at 60° C. for 15 minutes by using 30 ml of threefold SSC (26.28 g NaCl, 13.23 g sodium citrate, 1 l water) and 0.1% SDS. This treatment was repeated further twice. After the washing treatment, the film was dipped in threefold SSC containing 60 μg/ml salmon DNA, tenfold Denhalt solution (50 g ficoll, 50 g polyvinylpyrrolidone, 50 g bovine serum albumin, 500 ml water) and 0.1% sodium pyrophosphate and allowed to stand overnight at 60° C. After washing the membranes twice with 30 ml of a solution consisting of fourfold SSC (35.04 g NaCl, 17.64 g sodium citrate and 1 l water), 10 times of the Denhalt solution and 0.1% sodium pyrophosphate, it was hybridized overnight at 43° C. by using a synthetic nucleotide, 5'ATGGCGACGAAGGCC3' as a probe, labeled at the 5' end with $^{32}$P ($10^7$ cpm/μg). The synthetic nucleotide had the base sequence coding the N-terminus 5-amino acid moiety (Met, Ala, Thr, Lys, Ala) of h-SOD. After washing it twice, each for 15 minutes, at room temperature with fourfold SSC, tenfold of the Denhalt solution and 0.1% SDS, the membranes were dried and then subjected to autoradiography. As a result of screening of the transformants in the above-described manner, a clone having the h-SOD gene was obtained. It was named "pSOD1".

REFERENTIAL EXAMPLE 4

Determination of the base sequence of the h-SOD gene

After preparing pSOD1 DNA in a large amount by the lysozyme-SDS method and cesium chloride-ethidium bromide method [Maniatis, et al., "Molecular Cloning", 86–94, Cold Spring Harber (1982)], DNA fragments of about 700 bp containing the h-SOD gene was obtained by using restriction endonucleases "Pst I" and "Pvu II" (product of Takara Shuzo Co., Ltd.). Using restriction endonucleases "TthHB8I", "StuI", "HinfI", "RsaI", "FokI", "Sau3AI" (which are all products of Takara Shuzo Co., Ltd.) and "Fnu4HI" (NEB), a restriction map of the above fragment was prepared. The restriction map is illustrated in FIG. 2. Based on this restriction endonuclease map, the base sequence of the code region of the h-SOD polypeptide was determined by the Maxam-Gilbert method [Method Enzymol, 65, 449 (1979)]. Results are shown in FIG. 3. From the base sequence, the h-SOD gene was found to code 154 amino acids.

REFERENTIAL EXAMPLE 5

Expression of h-SOD in *E. coli*

(i) Using the EcoRI and BamHI sites of pIN-I-A2 which is one of expression vectors for *E. coli* [the same vector as pKEN 039 described in Japanese Patent Laid-Open No. 140800/1982; EMBO, J., 6, 771–775 (1982); obtained from State University of New York, 4.9 Kbp Amp[4]), the expression of h-SOD in *E. coli* was attempted based on the base sequence of the h-SOD gene determined in Referential Example 4. To 2 μl (0.1 μg) of a solution containing a 700 bp DNA fragment obtained by digestion of PstI and PvuII, 2 μl of 1M Tris-HCl (pH 8.0), 2.4 μl of 0.1M $MgCl_2$, 2 μl of 1M NaCl, 0.8 μl of 0.3M dithiothreitol, 2 μl of 5 mM dNTP, 3 units T4 of DNA polymerase (product of Takara Shuzo Co., Ltd.) and water were added to bring the total volume to 50 μl. After incubation of the mixture at 37° C. for 10 minutes, it was subjected to a phenol-chloroform treatment and ethanol precipitation, and the precipitate was washed and then dried under reduced pressure. It was dissolved with 70 μl of water, followed by addition of 6.5 μl of 1M Tris-HCl (pH 7.6), 10 μl of 0.1M $MgCl_2$, 10 μl of 10 mM ATP, 1.5 μl of 0.3M dithiothreitol, 1 μl of 5'-phosphated BamHI linker [1 μg CGGATCCG (product of Takara Shuzo Co., Ltd.) per μl] and 2 units of T4 DNA ligase. The resultant mixture was allowed to stand overnight at 22° C., followed by a phenol-chloroform treatment and ethanol precipitation. The precipitate was dissolved in 70 μl of an aqueous solution which contained 1 μg of a cloning vector, pACYC184 DNA [Journal of Bacteriology, 134, 1141 (1978); ATCC 37033] digested with "BamHI" (product of Takara Shuzo Co., Ltd.) and treated with 0.6 unit bacterial alkaline phosphatase (hereinafter abbreviated as "BAP"; product of Takara Shuzo Co., Ltd.). To this solution 10 μl of tenfold ligation buffer [0.5M Tris-HCl (pH 7.4), 0.1M $MgCl_2$, 0.1M dithiothreitol, 10 mM spermidine and 10 mM ATP] and 1 unit of T4 DNA ligase were added, water was added to bring the total volume to 100 μl, and the resultant mixture was then allowed to stand overnight at 4° C. After phenol-chloroform treatment, ethanol precipitation and washing and drying under reduced pressure, the resultant product was dissolved in 10 μl TE (pH 8.0). Using the thus-obtained DNA, the *E. coli* DH1 was transformed following the procedures (ii) and (iii) of Referential Example 2. A plasmid, from which DNA fragments containing the SOD gene were able to be cut out by digestion with BamHI, was obtained. The plasmid was named "pSOD5".

(ii) Water was added to 150 μl (100 μg) pSOD5 DNA, 18 μl tenfold BamH I digestion buffer [100 mM Tris-HCl (pH 8.0), 70 mM $MgCl_2$, 1M NaCl, 10 mM dithiothreitol] and 180 units BamH1 to bring the total volume to 180 μl and was then digested at 37° C. for 3 hours. A gel slice containing about 700 bp DNA fragments were cut out by electrophoresis in a 0.7% agarose gel. After extracting the DNA from the gel, it was subjected to a phenol-chloroform treatment for its purification, ethanol precipitated and washed, and then dried under reduced pressure. The DNA was dissolved in 44 μl TE (pH 8.0), to which 10 μl tenfold TthHB8I digestion buffer [100 mM Tris-HCl (pH 7.5), 100 mM $MgCl_2$, 1M NaCl, 10 mM dithiothreitol] and 10 μl (80 units) TthHB8I (product of Takara Shuzo Co., Ltd.) were added. The DNA was hydrolyzed at 37° C. for 3 hours and about 600 bp DNA fragments were separated by electrophoresis in a 0.7% agarose gel. After purifying the DNA fragments in the manner described above, they were dissolved in 100 μl water. The DNA fragments had cohesive ends, TthHB8I and BamHI, at both termini thereof and contained, on the side of TthHB8I, a base sequence coding the amino acids after the glutamic acid which is the 22th amino acid in the SOD polypeptide.

(iii) Besides, the following 12 oligo nucleotides were chemically synthesized for the expression of h-SOD.

```
5' AATTCTGATAAG      3'

GAGGTCAAAAAAATG

GCGACGAAGGCCG

TGTGCGTGCTGAAGGG

CGACGGCCCAGTGC

AGGGCATCATCAATTT

GACCTCCTTATCAG

CGTCGCCATTTTTTT

CACGCACACGGCCTT

GCCGTCGCCCTTCAG

ATGCCCTGCACTGG

CGAAATTGATG
```

To a 1 μl (1 μg) aliquot of each of these synthetic nucleotides, were added 5 μl of tenfold concentration linker kinase buffer [0.7M Tris-HCl (pH 7.6), 0.1M $MgCl_2$, 50 mM dithiothreitol], 1 μl of 50 mM ATP, 31 μl of water and 1 μl (10 units) of polynucleotide kinase (product of Takara Shuzo Co., Ltd.). The resultant mixture was incubated at 37° C. for 1 hour and at 85° C. for further 10 minutes and the cooled gradually. To a 25 μl aliquot of this reaction mixture, 10 μl of tenfold ligation buffer, 64 μl of water and 1 μl (2.8 units) of T4 DNA ligase (product of Takara Shuzo Co., Ltd.) were added. The resultant mixture was allowed to stand overnight at 4° C. Thereafter, the mixture was phenol-chloroform treated and the water layer was collected.

(iv) Besides, after incubating at 37° C. for 2 hours a liquid mixture of 3 μl (2 μg) of pIN-I-A2 vector, 3 μl of tenfold BamHI digestion buffer, 1 μl (20 units) of EcoRI, 2 μl (16 units) of BamHI and 21 μl of water, 5 μl of Tris-HCl (pH 8.0), 60 μl of water and 5 μl (0.6 unit) of BAP were added. The resultant mixture was incubated at 37° C. for further 1 hour. Thereafter, it was phenol-chloroform treated and the water layer was collected.

(v) Ten microliter aliquots of the thus-prepared DNA fragment solution containing the DNA coding the TthHB8I-BamHI h-SOD gene, solutions of the joined synthetic nucleotides and pIN-I-A2 vector were mixed, followed by addition of 3 μl of 3M sodium acetate and 66 μl of ethanol. After allowing the resultant mixture to stand at −70° C. for 15 minutes, a precipitate was collected by centrifugation. After drying it under reduced pressure, it was dissolved with 89 μl of water and 10 μl of tenfold ligation buffer and after an addition of 1 μl (2.8 units) of T4 DNA ligase (product of Takara Shuzo Co., Ltd.), the mixture allowed to stand overnight at 4° C. After phenol-chloroform treatment, ethanol precipitation, washing and drying, the DNA was dissolved in 10 μl TE (pH 8.0), and $E.\ coli$ DH1 which had been rendered competent in the above-described manner was transformed by it. The cells were spread on the LB agar medium containing 50 μg/ml ampicillin and then cultured overnight at 37° C. The thus-obtained h-SOD expression clone was named "pSOD6". The above steps are depicted in FIG. 4.

As a result of an EIA making use of an antibody against h-SOD, the $E.\ coli$ strain DH1 which carried pSOD6 was found to express 2 μg/ml (cultured cell broth) h-SOD when cultured overnight in the BHI culture medium.

(vi) Purification of h-SOD

After suspending 200 g of $E.\ coli$ with pSOD6 expressed thereon in 600 ml of a solution of Tris-HCl buffer (pH 7.6) which contained 1 mM $CuSO_4$, 1 mM $ZnSO_4$ and 50 mM saccharose, the resulting suspension was subjected to a supersonic treatment for 30 minutes by "Cell Disruptor 90" (trade name) manufactured by Branson, Inc. to lyse the cells. The lysate was added with 600 ml of a 3:5 mixed solvent of chloroform and ethanol and stirred at 4° C. for 15 minutes, and the resultant precipitate was removed by centrifugation. $K_2HPO_4$ (300 g) was dissolved in the supernatant and the resulting ethanol layer (500 ml) was chilled at −20° C. for 30 minutes. The resulting precipitate was discarded by centrifugation and the supernatant was condensed under reduced pressure in an evaporator. The thus-obtained condensate (300 ml) was then subjected to gel filtration by using a column (4.5×60 cm) packed with "Sephadex G-25 gel" (trade name; product of Pharmacia AB) which had been equilibrated with a solution containing 50 mM saccharose and 25 mM phosphate buffer (pH 7.8), whereby the condensate was substituted for the solution. Ten grams of DE52 (trade name; product of Whatman Company) were added and the resultant mixture was agitated at 4° C. for 30 minutes, so that impurities were adsorbed and then removed on a glass filter. After dialyzing the filtrate against 2.5 mM phosphate buffer (pH 6.5) containing 50 mM saccharose, it was passed through a column (1.6×20 cm) packed with "DEAE-Sepharose CL-6B" (trade name; product of Farmacia AB) which had been equilibrated in advance with the same buffer, so that the recombinant h-SOD was adsorbed. The column was then washed with the same buffer and the concentration of the phosphate buffer was increased linearly from 2.5 mM to 50 mM, thereby eluting the recombinant h-SOD. Since SOD activities were observed in two separate peaks, the eluate fraction corresponding to the first peak was collected and lyophilized. The thus-lyophilized powder was dissolved in 10 ml of distilled water and poured in a column (4.5×80 cm) packed with "Sephadex G-100" (trade name; product of Farmacia AB) which had been equilibrated with 10 mM Tris-HCl buffer (pH 7.0) containing 50 mM saccharose, whereby the lyophilized powder was purified by gel filtration. The activities of the h-SOD obtained in the above manner were 3,000–3,500 units per mg of SOD. It showed a single band upon its electrophoresis.

EXAMPLE 1

Conversion of Cys (111) of h-SOD to Ser

Site-specific mutagenesis was effected in accordance with the Vlasuk-Inouye method ["Experimental Manipulation of Gene Expression", 291–303, Academic Press (1983)].

(i) 5 μg cc (closed circular) DNA of pSOD6 (5.6 kb, Ap$^r$) which is a plasmid containing the h-SOD gene was dissolved with 300 μl of a solution containing 50 mM Tris-HCl (pH 7.5), 10 mM $MgCl_2$, 10 mM NaCl and 0.15 mg/ml EtBr. Under light-shielded conditions, 200 units BamHI (product of Takara Shuzo Co., Ltd.) were added, followed by incubation at 37° C. for 90 minutes. 10 μl of 0.5M EDTA (pH 8.0) and 300 μl of phenol-chloroform were added and mixed. A water layer was collected by centrifugation, to which 30 μl of 3M sodium acetate and 660 μl of ethanol were added. The resultant mixture was allowed to stand at −70° C. for 10 minutes, and a precipitate was collected by centrifugation and dried to solid under reduced pressure. It was then dissolved in 40 μl of a solution containing 66 mM Tris-HCl (pH 8.0), 0.66 mM $MgCl_2$ and 10 mM dithiothreitol, followed by an addition of 50 units of exonuclease III (product of PL-Biochemical Company). The resultant mixture was incubated at 37° C. for 90 minutes. After an addition of 2 μl of 0.5M EDTA (pH 8.0) and phenol-chloroform treatment, the DNA was collected by ethanol precipitation and was then dried to solid under reduced pressure. It was dissolved in 50 μl of a solution containing 200 mM NaCl, 13 mM Tris-HCl (pH 7.6), 9 mM $MgCl_2$ and 10 mM dithiothreitol to obtain Liquid (1). Besides, 1 μg synthetic nucleotide 5′ AGACCATTCCATCATTG 3′ (note: the 9-site C is G in the original SOD gene) was dissolved in 10 μl of a solution containing 50 mM Tris-HCl (pH 7.6), 10 mM $MgCl_2$, 5 mM dithiothreitol, 0.1 mM spermidine, 0.1 mM EDTA and 5 mM ATP, to which 3.2 units of T4 nucleotide kinase (product of Takara Shuzo Co., Ltd.) were added. They were reacted at 37° C. for 1 hour to obtain Liquid (2). A 50 μl aliquot of Liquid (1) and a 5 μl aliquot of Liquid (2) were mixed, heated at 100° C. for 3 minutes and chilled quickly. The resultant mixture was then left over at 4° C. for 2 hours, followed by addition of 7 μl of 5 mM dNTP, 2 μl of 50 mM ATP, 3 μl (6 units) of T4 DNA polymerase (product of Takara Shuzo Co., Ltd.), 3 μl (4.2 units) of T4 DNA ligase (product of Takara Shuzo Co., Ltd.) and 30 μl of water. After allowing the resultant mixture to stand overnight at 12.5° C., it was treated by phenol and ethanol precipitate was collected. The DNA was thereafter dried to solid under reduced pressure. After dissolving the DNA in 10 μl of TE (pH 8.0), the $E.\ coli$ strain DH 1 was transformed to obtain ampicillin resistant transformant.

(ii) About these transformants, a screening of clones hybridized with the synthetic nucleotide which was labeled with $^{32}P$ at the 5′-end ($10^7$ cpm/μg) was carried out using the colony hybridization method. The clone obtained in the above manner was named "pSOD14". Similar to the above-described procedures, the base sequence of pSOD14 DNA was then determined by the Maxam-Gilbert method. As a result, it was confirmed that the Cys-coding TGC had been changed to the Ser-coding TCC. The base sequence of the plasmid pSOD14 DNA is shown in FIG. 1.

(iii) The *E. coli* strain DH1 containing pSOD14, which had been obtained in the above-described manner, was cultured overnight at 37° C. by the rotation culturing method on the BHI culture medium (pH 7.4±0.2).

After completion of the culture, the cultured broth was centrifuged at 15,000 rpm for 30 seconds to harvest the cells.

(iv) The collection of the recombinant h-SOD in its purified form from the above-obtained cells was conducted in accordance with the method proposed by I. Fridovich, et al. [J. Biol. Chem., 244(22), 6049–6055 (1969)]. Namely, after suspending 200 g of the cells in 600 ml of a solution containing 50 mM Tris-HCl buffer (pH 7.6) which contained 1 mM $CuSO_4$, 1 mM $ZnSO_4$ and 50 mM saccharose, a supersonic treatment was applied for 30 minutes by "Cell Disrupter 900" manufactured by Branson Company so that the cells were lysed. The lysate was added with 0.75 volume of a 3:5 mixture of chloroform-ethanol and the resultant mixture was stirred at 4° C. for 15 minutes and then centrifuged to remove the precipitate. In the supernatant, dipotassium hydrogenphosphate was dissolved to a concentration of 300 g/l so that the ethanol layer (about 500 ml) was salted out. The ethanol layer was collected by centrifugation and chilled at −20° C. for 30 minutes. The crystallized precipitate was removed by centrifugation and the supernatant (about 300 ml) was concentrated under reduced pressure in an evaporator. The thus-concentrated solution was subjected to gel filtration on a column (4.5×60 cm) packed with "Sephadex G-25" gel (product of Farmacia AB) equilibrated with 25 mM phosphate buffer (pH 7.8), whereby the solution was substituted for the 25 mM phosphate buffer. To the concentrated solution, 10 g of DE52 (product of Whatman Company) was added and the resultant mixture was stirred at 4° C. for 30 minutes. Impurities were adsorbed and the solution was then filtered. After dialyzing the filtrate against 2.5 mM phosphate buffer (pH 6.5) containing 50 mM saccharose, it was poured in a column (1.6×20 cm) packed with "DEAE-Sepharose CL-6B" gel (product of Farmacia AB) and equilibrated with the same buffer, so that the recombinant h-SOD was adsorbed. The column was then washed with the same buffer and the concentration of the phosphate buffer was increased linearly from 2.5 mM to 50 mM, thereby eluting the recombinant h-SOD. Since SOD activities were observed in two separate peaks, these active fractions were separately pooled and lyophilized. Lyophilized powder of one of the two active fractions, which was eluted first, was dissolved in 10 ml distilled water and was poured in a column (4.5×80 cm) packed with "Sephadex G-100" (product of Farmacia AB) equilibrated with 10 mM Tris-HCl buffer (pH 7.0) which contained 50 mM saccharose, whereby the lyophilized powder was purified by gel filtration. The activities of the recombinant h-SOD obtained by the above procedure were determined by the above-described method proposed by Fridovich, et al. Per mg of SOD, 3000–3600 units were exhibited. The recombinant h-SOD was at least equal in specific activities and physicochemical properties to h-SOD purified from human red blood cells.

This recombinant h-SOD was confirmed to be represented by the general formula (II) in which $X_1$, $X_2$ and $X_3$ mean a hydrogen atom, Cys and Ser respectively and $Y_1$ and $Y_2$ are 2 respectively (measured by EIA and atomic absorption spectrophotometry.

Figure 6:
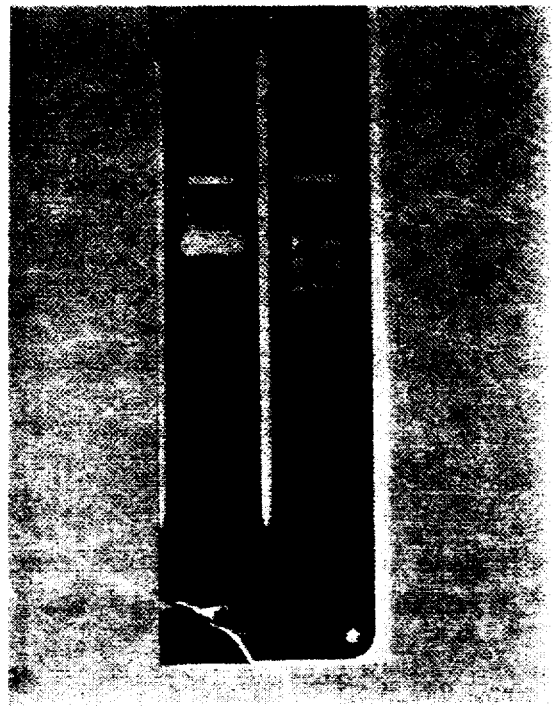
FIG. 6 illustrates an electropherogram of an h-SOD analogous recombinant polypeptide obtained in Example 1.

(v) From 1 ml of overnight culture of *E. coli* strain DH1 carrying pSOD14 [*Escherichia coli* DH1 pSOD14; FERM BP-1696] in the BHI culture medium, cells were collected by centrifugation. After removal of the supernatant, the cells were added with 1 ml of 50 mM Tris-HCl buffer (pH 7.6) which contained 1 mM $CuSO_4$, 1 mM $ZnSO_4$ and 50 mM saccharose. Under ice cooling, the resultant mixture was subjected to a supersonic treatment for 5 minutes ("Handy Sonic UR-20P" manufactured by Tomy Corporation was used) so that the cells were lysed. A 1 µl aliquot of the lysate was dropped in the sample slots of an agarose gel film 0product of Corning Company; "Universal") which had in advance equilibrated by 20 mM tris-glycine buffer (pH 8.45). After conducting electrophoresis at 250 V for 20 minutes in a 20 mM tris-glycine buffer (pH 8.45), the film was immersed for 2 minutes in a 5 mg/ml nitroblue tetrazolium solution which contained 0.1 mM riboflavin. The solution was allowed to drip off from the film. After dipping the film for 1 minute in a 1% tetramethylethylene diamine solution, the solution was allowed to drip off from the film. The film was caused to produce a color in white light until a contrast appears with a white background in a gel. After production of the color, the unreacted reagent was washed away with distilled water and the film was then dried. Results are shown in FIG. 6, in which an area having h-SOD activities did not produce the color but the other area was turned to a purple color. As apparent from this drawing, the width of the active band was narrow in the case of the recombinant h-SOD of this invention (lefthand side; Ser at the 111th site of the amino acid sequence) which was obtained from the cultured cell broth of the *E. coli* strain carrying the plasmid pSOD14. It is therefore appreciated that the recombinant h-SOD is hard to yield isomers and is also stable On the other hand, h-SOD obtained from *E. coli* carrying the plasmid pSOD6 had a broad band and produced many isomers.

(vi) Stability of h-SOD and recombinant h-SOD on standing:

One milligram aliquots of h-SOD obtained in the procedure (vi) of Referential Example 5 and the recombinant h-SOD obtained in Example 1 were separately dissolved in portions of a 0.1M phosphate buffer (pH 7.0) containing 50 mM of saccharose and then left over at room temperature for 1 week. The resulting solutions were subjected to isoelectric focusing. Each of h-SOD and the recombinant h-SOD showed a single peak at an isoelectric point (pI) of 5.0 at the beginning of the experiment. This peak will hereinafter be designated commonly as "$S_0$". As a result of the experiment, four isomers having different isoelectric points (pI=5.1, 4,9, 4.85 and 4.8) were formed. The peaks corresponding to these isomers will hereinafter be designated as $S_{-1}$, $S_1$, $S_2$ and $S_3$ respectively. The proportion of the starting h-SOD ($S_0$) dropped to about 70%. In the recombinant h-SOD, an isomer was formed at pI=4.9. The peak corresponding to this isomer will hereinafter be designated as "$S_1$. The proportion of this isomer was however as low as 7.9% and more than 90% of the recombinant h-SOD was hence allowed to remain. Although $S_1$ had comparable activities with $S_0$, the activities of $S_2$ were lower than those of $S_0$. The activities of $S_3$ were less than one-half of those of $S_0$ and $S_{-1}$ had substantially no activities. Accordingly, significant improvements in stability in both structure and enzymatic activities were confirmed as a result of the conversion of h-SOD to the recombinant h-SOD.

| | | Compositions of h-SOD and recombinant h-SOD after 1 Week | | | | |
|---|---|---|---|---|---|---|
| Isomer pI | | $S_0$ 5.0 | $S_1$ 4.9 | $S_2$ 4.85 | $S_3$ 4.8 | $S_{-1}$ 5.1 |
| h-SOD | 0 hour | 100.0% | 0% | 0% | 0% | 0% |
| | 1 week | 71.0% | 20.4% | 4.0% | 1.0% | 3.5% |
| Recom. h-SOD | 0 hour | 100.0% | 0% | 0% | 0% | 0% |
| | 1 week | 92.1% | 7.9% | 0% | 0% | 0% |

EXAMPLE 2

In the same manner as in Example 1, pSOD35 was obtained by using a nucleotide 5' GAGACCATAC-CATCATT 3' synthesized on the side. In addition, pSOD36 was also obtained from an experiment in which the synthetic nucleotide 5' GAGACCATG-CCATCATT 3' was used on pSOD14 obtained in Example 1. In the h-SODs coded respectively by pSOD35 and pSOD36, the Cys at the 111 site had been changed to Thr and Ala respectively. The h-SODs produced by E. coli DH1 containing pSOD35 and pSOD36 respectively were both recombinant h-SODs stabilized as proteins and capable of showing SOD activities similar to Example 1.

Incidentally, recombinant h-SODs corresponding respectively to the synthetic nucleotides shown above in Table 1 can be obtained if the above procedures are practised by using synthetic nucleotides in stead of the above-described synthetic nucleotide.

EXAMPLE 3

To 100 μg (100 μl) pSOD14 DNA obtained in Example 1, were added 18 μl of tenfold BamHI digestion buffer [100 mM Tris-HCl (pH 8.0), 70 mM $MgCl_2$, 1M NaCl, 10 mM dithiothreitol], 120 units (10 μl) BamHI (product of Takara Shuzo Co., Ltd.) and 52 μl water. After reacting them at 37° C. for 2 hours, about 700 bp DNA fragments were extracted, purified and converted into a dry state in the same manner as that described above by electrophoresis in a 0.7% agarose gel. The thus-obtained DNA was dissolved in 44 μl of TE (pH 8.0), followed by addition of 6 μl of tenfold TthHb8I digestion buffer [100 mM Tris-HCl, 100 mM $MgCl_2$, 1 mM NaCl, 10 mM dithiothreitol) and 80 units (10 μl) TthHB8I (product of Takara Shuzo Co., Ltd.) so as to hydrolyze the DNA at 37° C. for 3 hours. About 600 bp DNA fragments were isolated and purified in the same manner as described above, followed by their dissolution in 100 μl of water. Besides, pSOD53 was also obtained in exactly the same manner as described in Referential Example 5(v) by using 5' TGTCCGTGCTGAAGGG 3' and 5' CACG-GACACGGCCTT 3' in lieu of 5' TGTGCGTGCTGAAGGG 3' and 5' CACG-CACACGGCCTT 3' among the 12 strands of the synthetic nucleotides employed in Referential Example 5(iii). As a result of determination of the base sequence of the DNA of pSOD53 in the aforementioned manner, it was confirmed that TGC, which had coded Cys at the 6th and 111th sites, had been both changed to TCC.

In view of results of an electrophoretic analysis in agarose, the recombinant h-SOD which had been obtained from the E. coli strain DH1 carrying pSOD53 in the same manner as in Example 1 was found to be stable like the recombinant h-SOD produced by the E. coli strain DH1 carrying pSOD14.

EXAMPLE 4

(i) An h-SOD gene cloning plasmid was prepared by modifying a cloning plasmid pSV2-dhfr [product of BRL Company; Mol. & Cell. Biol. 1, 854(1981)] which contained the SV40 promoter of the gene of the mouse folic acid reductase. pSOD14 was digested by the restriction endonucleases XbaII and BamHI to isolate the h-SOD gene Fragments of this gene were then ligated by T4 ligase with a vector which had been obtained by digestion of pSP64 plasmid [product of Amasham Company; Nucleic Acid Res. 12, 7035 (1984)] with the restriction endonucleases XbaI and BamHI, thereby obtaining pSP64-h-SOD plasmid. By digestion of pSP64-h-SOD with the restriction endonucleases HindIII and BamHI, DNA fragments containing the h-SOD gene were isolated again. Finally, the above-mentioned HindIII-BamHI fragments were ligated with T4 ligase on the vector which had been obtained by digestion of pSV2-dhfr plasmid with HindIII and BglII so that a plasmid pSV2-h-SOD for the expression of the h-SOD gene in mammalian cells was obtained.

(ii) The introduction (transformation) of the thus-obtained plasmid DNA in cells was done by the DNA-calcium phosphate precipitation method [TANPAKU-SHITSU. KAKUSAN.KOSO (Proteins, Nucleid Acids & Enzymes), Special Edition, 27, 340(1984)]. Sterile air was blown into 1 ml of a solution which was composed of 20 mM HEPES buffer (pH 7.10), 50 mM NaCl, 0.7 mM sodium phosphate, 120 mM CaCl and pSV2-h-SOD plasmid (10 μg/ml), so that a cloudy DNA-calcium phosphate solution was formed. It was then added to 50 Petri dishes (diameter: 8 cm), in which COS cells [Cold Spring Harbar, Symp. Quant. Biol., 44, 293(1979)] had been multiplied in DMEM medium + 10% neonatal calf serum. After culturing the COS cells at 37° C. for 48 hours in an incubator which contained 5% $CO_2$, the cells were harvested and then suspended in 10 mM phosphate buffer (pH 7.4). The cells were thereafter disrupted by "Polytron" and then centrifuged at 15,000 rpm for 10 minutes to obtain a supernatant. The supernatant was isolated by electrophoresis in agarose and a band corresponding to h-SOD was activated and stained to investigate its mobility. Results are summarized in the following table.

| | Mobility (cm) | |
|---|---|---|
| | Anode side | Cathode side |
| Supernatant of COS cells transformed by pSV2-h-SOD | 2.2[a] | 0.9[b] |
| SOD obtained from human red blood cells | 2.2[a] | |
| Supernatant of untreated COS cells | | 0.9[b] |

[a]h-SOD
[b]Monkey SOC

EXAMPLE 5

Expression of h-SOD in yeast (i) Preparation of cloning plasmid (1) 1 μg plasmid pSOD14 of Example 1 and 1 μg pUC19 [purchased from Takara Shuzo Co., Ltd; Yanisch-Perron, C., et al., Gene (1985) 33, 103–119] were digested at 37° C. for 2 hours in separate containers by using 50 μl XbaI buffer [6 mM $MgCl_2$, 6 mM Tris-HCl, 100 mM NaCl, pH 7.4] which contained the restriction endonucleases XbaI and BamHI (purchased from Takara Shuzo Co., Ltd.; all restriction endonucleases and other enzymes employed for DNA modification and ligation, which will hereinafter be referred to, were produced by the same company unless otherwise specifically indicated), each, in an amount of about 10 units. The XbaI-BamHI digest of pUC19 were phenol treated, ethanol precipitated, ethanol washed and then dried. The precipitate was thereafter dissolved in 10 μl TE [10 mM Tris-HCl (pH 8.0)-1 mM EDTA solution], to which were added 10 μl fivefold BAP buffer [250 mM Tris-HCl, pH 8.3], 29 μl sterile distilled water and 1 μl (about 0.4 unit) bacteria (*E. coli*) origin alkaline phosphatase [bacterial alkaline phosphatase] (hereinafter abbreviated as "BAP"). The resultant mixture was incubated at 65° C. for 30 minutes (this is an enzymatic treatment for the removal of the phosphoric acid at the 5'-terminus and will hereinafter be called "BAP treatment"). The BAP-treated XbaI-BamHI digest of pUC19 and XbaI-BamHI digest of pSOD14 were subjected to electrophoresis in a 1% (w/v) agarose gel. The resultant gel was dipped in a solution which had been obtained by adding ethidium bromide at a concentration of 0.5 μg/ml to an electrophoretic buffer [0.04M Tris-acetate, 2 mM EDTA (pH 8.1)] (hereinafter called "EtBr staining solution"). The gel was left over for 20 minutes there. The gel was then pulled out and placed on a table, where it was exposed to long-wavelength ultraviolet rays (366 nml radiated from Model UVL-56 manufactured by Ultraviolet Products Inc.) to visualize the DNAs. Judging from a DNA fragment size marker of the HindIII restriction enzyme digest of λ phage DNA which was subjected concurrently to electrophoresis, gel pieces which contained the XbaI-BamHI DNA of about 2680 base pairs (hereinafter abbreviated as "bp") and XbaI-BamHI DNA fragments of about 700 bp respectively were sliced out by anatomical scalpels from the electrophoresis lane of the pUC19 digest and pSOD14 digest respectively. These gel pieces were placed in separate dialysis tubes each of which contained about 0.4 ml of the above-described electrophoretic buffer. After closing both ends of each of the tubes, the tube was placed standstill in a horizontal electrophoretic bath filled with the above-mentioned electrophoretic buffer. It was then subjected to electric elution at 200 V for 30 minutes. One end of the dialysis tube was opened and the buffer containing the eluted DNA was transferred from the tube into an Eppendorf tube.

The thus-obtained eluates, which contained these fragments, were respectively phenol treated, ethanol precipitated, ethanol washed and dried. The resultant precipitates were separately dissolved in 10 μl TE. A 2 μl aliquot of the above-prepared solution, which contained about 2680 bp fragments obtained from pUC19, was added to a 2 μl aliquot of the above-prepared solution of about 700 bp fragments obtained from pSOD14, 1 μl tenfold ligation buffer [described already in Referential Example 5] and 1 μl (about 350 units) T4 DNA ligase. The resultant mixture was allowed to stand overnight at 4° C. By using the thus-prepared ligation liquid, the *E. coli* strain DH1 was transformed in accordance with the procedures (ii) and (iii) of Referential Example 2.

(2) Four transformants were chosen at random from the resultant transformants. They were cultured overnight at 37° C. in a liquid BHI culture medium (ampicillin content: 50 μg/ml) and a plasmid was obtained from the cultured cell broth in the following manner.

Namely, a 1.5 ml aliquot of the cultured cell broth which contained the cells cultured in the liquid medium was transferred in an Eppendorf tube (product of Eppendorf Company) and centrifuged at 15000 rpm and 4° C. for 30 seconds by a small centrifuge ("MR-15A", manufactured by Tomy Seiko K.K.), and the resultant supernatant was thrown away. To the cells collected on the bottom of the tube, 100 μl lysozyme solution [20% glucose, 50 mM Tris-HCl (pH 8.0), 1 mM EDTA (pH 8.0); a solution obtained by dissolving chicken egg white origin lysozyme (product of Sigma Company) in an amount of 2 mg per ml of the solution] was added to suspend the cells. After holding the container standstill for 20 minutes in ice water, 0.2N NaOH and 200 μl 1% SDS (sodium dodecylsulfate) were added further. The resultant mixture was stirred thoroughly and then left over in ice for 5 minutes. Thereafter, 150 μl 3M sodium acetate (pH 4.8) was added, and the resultant mixture was stirred thoroughly and left over in ice for 3 hours. The mixture was then centrifuged at 15000 rpm and 4° C. for 10 minutes by the above centrifuge and the resultant supernatant was transferred in a separate Eppendorf tube. 1.2 ml ethanol was added, mixed thoroughly, and then allowed to stand at −20° C. for 20 minutes. The mixture was then centrifuged at 15000 rpm and 4° C. for 10 minutes by the above centrifuge and the resultant supernatant was thrown away. In order to wash the precipitate, 1 ml anhydrous ethanol was added to the container. The resultant mixture was centrifuged at 15000 rpm and 4° C. for 30 seconds by the above centrifuge and the supernatant was again thrown away. The liquid still remaining in the container and consisting principally of ethanol was evaporated at room temperature for 10 minutes under reduced pressure by a vacuum pump. A small amount of solid (which contained the plasmid DNA) occurred on the bottom of the container was obtained, to which 50 μl TE (pH 8.0) was added to dissolve same. A 2 μl aliquot of the TE solution was digested at 37° C. for 2 hours in 20 μl XbaI buffer which contained 2.5 units XbaI, 2.5 units BamHI and 1 μg bovine spleen origin ribonuclease (product of Farmacia AB; hereinafter abbreviated as "RNase"). The resultant digest was subjected to electrophoresis in 0.7% agarose. As a result, the appearance of about 700 bp DNA fragment from each of the four plasmids was confirmed. One of these four plasmids was named "pUC19-SOD14".

The strain DH1 retaining this plasmid was named "DH1/pUC19-SOD14". This bacterium was cultured in a large quantity to obtain the DNA. Namely, DH1/pUC19-SOD14 was cultured overnight at 37° C. in 100 ml liquid BHI culture medium in which 50 μg/ml ampicillin was contained. The cultured cell broth was centrifuged at 5000 rpm and 4° C. for 10 minutes by using "No.17N Rotor" manufactured by Tomy Seiko K.K. and the resulting supernatant was thrown away. Added to the centrifuge tube was 20 ml 20 mM Tris-HCl (pH 7.5) to suspend the cells on the bottom. The suspension was transferred in a separate container, followed by its centrifugation at 5000 rpm and 4° C. for 10 minutes by the same "No.4 Rotor" manufactured by Tomy Seiko K.K. The supernatant was thrown away and cells were collected on the bottom. The cells were then suspended in 2 ml lysozyme solution and the container was left over in ice for 30 minutes. After adding 0.2N NaOH and 4 ml 1% SDS solution and thoroughly stirring the resultant mixture, the container was left over in ice for 20 minutes. 3 ml 3M sodium acetate (pH 4.8) was then added and the resultant mixture was thoroughly stirred, and the container was left over in ice for 2 hours. Using the above-mentioned "No.4 Rotor", the above-prepared mixture was centrifuged at 14000 rpm and 4° C. for 10 minutes and the resulting supernatant was transferred in a separate container. Added to the supernatant were 2.5 volumes of anhydrous ethanol. After cooling the resultant solution at −20° C. for 20 minutes, it was centrifuged at 14000 rpm and 4° C. for 10 minutes by the above "No.4 Rotor". The resulting supernatant was thrown away, and the precipitate which occurred on the wall and bottom of the container was dissolved in 4 ml TE, followed by an addition and dissolution of 4.2 g cesium chloride. 0.5 ml of 10 mg/ml ethidium bromide solution was added further. The resultant mixture was transferred in a "Quick Seal" centrifuge tube manufactured by Beckman Company and its upper end opening was closed by a "Tube Sealer" manufactured by Beckman Company. It was then centrifuged at 50000 rpm and 15° C. for 16 hours by a "VTi 65.2 Rotor" manufactured by the same company. The tube was gently removed from the rotor and in a dark room, the second band from the top in the central part out of the bands observed in the orange color upon exposure to the long-wavelength ultraviolet rays was collected separately while the internal liquid was allowed to drip out through a hole formed by an injection needle through the bottom of the centrifuge tube.

The liquid containing the above-collected band was added at room temperature with n-butanol in an amount of 1 volume to 3 volumes. The resultant mixture was shaken and mixed to extract and remove ethidium bromide intercalated in the DNA. After repeating this extraction and removal operation 5 times, the lower layer, i.e., water phase was transferred in a dialysis tube in order to get rid of cesium chloride. Using 500 ml TE as an outer solution, the water phase was dialyzed at 4° C. for 2–30 hours while replacing the outer solution 3 times in the course of the dialysis. The inner solution of the dialysis tube was then transferred into an Eppendorf tube, to which the same amount of TE-saturated phenol was added. The resultant mixture was stirred thoroughly and centrifuged at room temperature and 15000 rpm for 30 seconds by a small centrifuge, and of the resultant two layers, the upper layer was collected separately. The same amount of diethyl ether was added and the resultant mixture was stirred thoroughly. The upper ether layer was then thrown away. This ether extraction (for the removal of phenol) was conducted three times in total. The remaining ether was removed by vacuum evaporation. Then, per 400 µl liquid, were added 10 µl 1M MgCl₂ and 40 µl 5M potassium acetate, followed by a further addition of 1 ml anhydrous ethanol. The resultant solution was chilled and lyophilized at −110° C. for 10 minutes. It was then centrifuged at 4° C. and 15000 rpm for 10 minutes by a small centrifuge, the supernatant was thrown away, 1 ml anhydrous ethanol was added and the resultant mixture was centrifuged for 30 seconds under the same conditions. The precipitate was dried to solid under reduced pressure, thereby obtaining a solid matter. The solid matter was then dissolved in 400 µl TE. In this manner, pUC19-SOD14 plasmid was obtained in a large amount.

(3) Thereafter, 1 µg of the DNA of pAM82 (furnished courteously from Dr. Kenichi Matsubara, the Cytoengineering Center, Osaka University; described in Japanese Patent Laid-Open No. 36699/1984; FERM-P-8838) was digested by about 10 units restriction endonuclease PvuII at 37° C. for 2 hours in 20 µl M buffer [10 ml Tris-HCl, 10 mM MgCl₂, 1 mM DTT and 50 mM NaCl, pH 7.5). The resultant mixture was phenol treated, ethanol precipitated, ethanol washed and then dried. The thus-obtained precipitate was digested again at 37° C. for 2 hours in 20 µl of H buffer (10 mM Tris-HCl, 10 mM MgCl₂, 1 mM DTT and 100 mM NaCl; pH 7.5) which contained about 10 units of the restriction endonuclease XhoI. After subjecting the digest to phenol treatment, ethanol precipitation, ethanol washing and drying, the resultant precipitate was dissolved in 10 µl TE, to which 10 µl fivefold BAP buffer (described above), 29 µl sterile distilled water and 1 µl (about 0.4 unit) BAP were added. A BAP treatment was then conducted at 65° C. for 30 minutes. The thus-treated solution will be called "pAM82 PvuII-XhoI/BAP solution". By about 10 units of the restriction endonuclease SalI, a 1 µg aliquot of pUC19-SOD14 plasmid DNA obtained before was digested at 37° C. for 2 hours in 20 µl H buffer. After phenol treatment, ethanol precipitation, ethanol washing and drying, the digest was digested again by about 10 units of the restriction endonuclease SmaI at 30° C. for 2 hours in 20 µl SmaI buffer (10 mM Tris-HCl, 7 mM MgCl₂, 20 mM KCl, 7 mM 2-mercaptoethanol, pH 8.0). The resultant digest and "pAM 82 PvuII-XhoI/BAP solution" were respectively subjected to electrophoresis in a 1% agarose gel, whereby pUC19-SOD14 origin SalI-SmaI DNA fragments of about 700 bp and pAM82 origin PvuII-XhoI DNA fragments of about 10 kilo bp were obtained by electric elution. After the eluates containing these DNA fragments respectively were subjected to phenol treatment, ethanol precipitation, ethanol washing and drying, the resulting precipitates were separately dissolved in 10 µl TE. 2 µl of each of the two types of DNA fragment solutions, 4 µl sterile distilled water, 1 µl tenfold ligation buffer and 1 µl (about 350 units) T4 DNA ligase were added together and then allowed to stand overnight at 4° C. Using this ligation liquid, the *E. coli* strain DH 1 was transformed in accordance with the procedures (ii) and (iii) of Referential Example 2. Two of the transformants thus-obtained were cultured overnight at 37° C. in the BHI liquid culture medium which contained 50 µg/ml ampicillin. From the cultured cells, the solution containing the plasmid DNA was obtained in the same manner as that described above. 2 µl aliquots of the solution were added separately to H buffer containing 2.5 units AatI and 1 µg RNase and to H buffer containing 2.5 units BamHI and 1 µg RNase. Each of the buffers was employed in such an amount that the final volume reached 20 µl. The plasmid DNA was digested by the respective restriction endonucleases at 37° C. for 2 hours. The resultant digests were subjected to electrophoresis in a 0.7% agarose gel. As a results, it was confirmed that in connection with the plasmids of both strains, fragments exhibiting the same mobility as the DNA fragments of about 0.5 kbp obtained by the AatI-BamHI digestion of pUC19-SOD14 occurred only in the digest obtained by both restriction endonucleases AatI and BamHI. One of these plasmid was named "pTJ102-SOD14".

Figure 7:
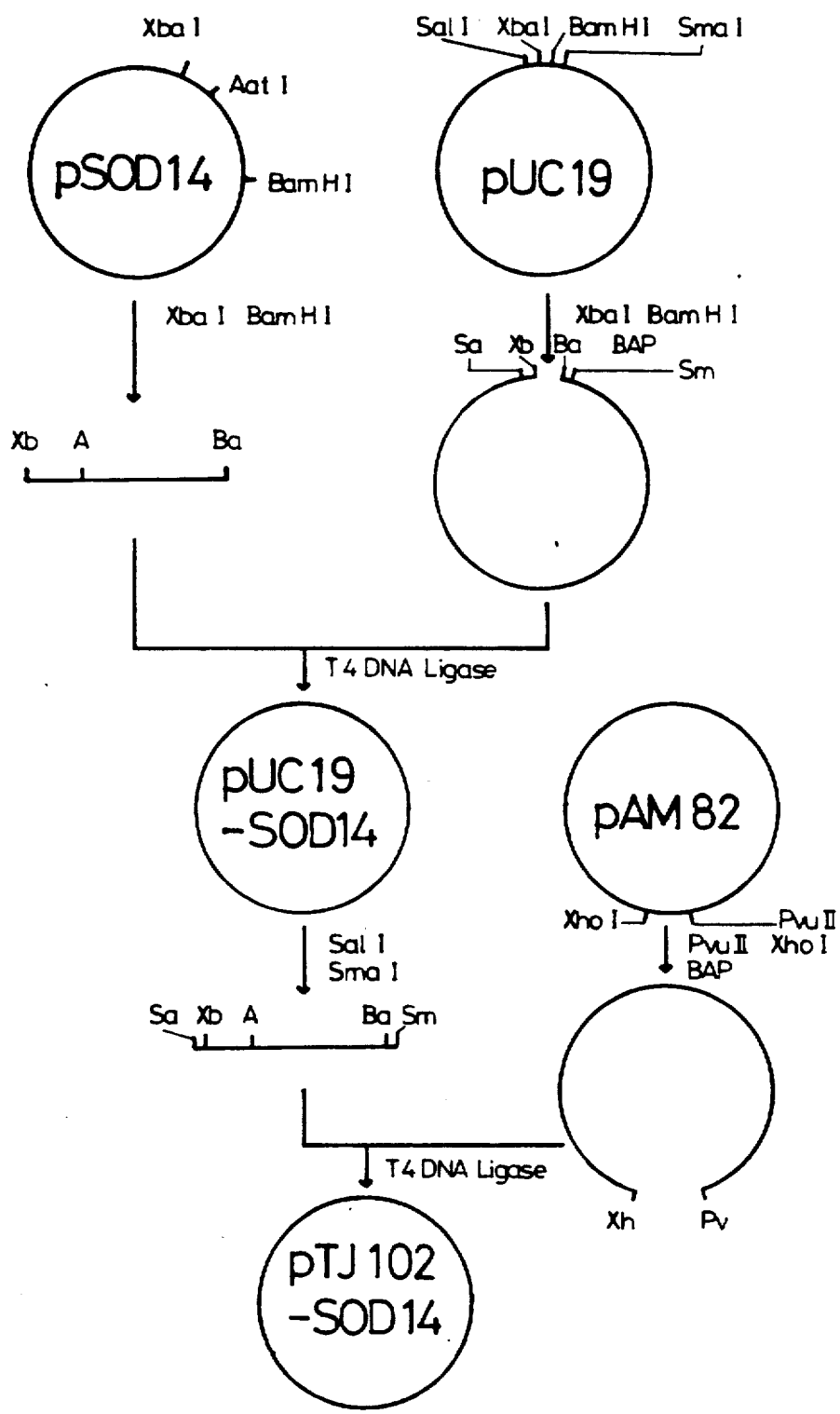
FIG. 7 is a simplified flow chart of recombination for the construction of a plasmid pTJ102-SOD14.

The flow chart of the above procedures is shown in FIG. 7.

(ii) Preparation of transformed yeast
As a yeast strain, *Saccharomyces cerevisiae* AH22 [a leu2 his4 can1 (cir+)] [furnished courteously from Dr.

Kenichi Matsubara, the Cytoengineering Center, Osaka University; disclosed in Japanese Patent Laid-Open No. 36699/1984; FERM P-8840] was employed. It was inoculated on 3 ml YPD culture medium (2% polypeptone, 1% yeast extract, 2% glucose), cultured overnight at 30° C., and centrifuged to harvest cells. The cells were suspended in 1 ml of prepared protoplast solution [50 μg/ml zymolyase-100T (product of Seikagaku Kogyo Co., Ltd.), 100 mM citrate buffer (pH 5.8), 10 mM EDTA, 1M sorbitol] and the resultant suspension was left over at 30° C. for 1 hour. After collecting the cells, they were washed twice with 1 ml of 1M sorbitol solution which contained 10 mM $CaCl_2$. The thus-washed cells were then suspended in 0.1 ml of the solution. About 5 μg (5 μl) pTJ102-SOD14 was added to a 50 μl aliquot of the suspension. The resultant mixture was allowed to stand at room temperature for 15 minutes, followed by an addition of 1 ml PEG solution [20%(w/v) PEG 4000, 10 mM Tris-HCl (pH 7.0), 10 mM $CaCl_2$]. The resultant suspension was left over at room temperature for 15 minutes. After collecting the cells, they were suspended in 0.1 ml 1M sorbitol and then added to 5 ml of a melted regeneration agar [1M sorbitol, 3% agar, and "Leu minus COM" {0.17% yeast nitrogen base, 0.5% ammonium sulfate, 2% glucose, 20 μg/ml adenine sulfate, 20 μg/ml L-arginine.HCl, 20 μg/ml L-histidine.HCl, 20 μg/ml L-methionine, 20 μg/ml L-tryptophane, 20 g/ml uracil, 30 μg/ml isoleucine, 30 μg/ml L-lysineHCl, 30 μg/ml L-tyrosine, 50 μg/ml L-phenylalanine, 150 g/ml L-valine}] which had been maintained at 45° C. The thus-prepared suspension was spread on a plate for its culture. From the 3rd day, a transformant equipped with the L-leucine non-auxotrophism became visible. This is attributed to the retention of plasmid pTJ102-SOD14 by the yeast strain AH22. This transformed yeast was named "AH22/pTJ102-SOD14". Similarly, in order to indicate a transformant obtained as a result of transformation of AH22 by a certain plasmid, the transformant will hereinafter be designated as "AH22/name of plasmid employed". For example, AH22 harboring pAM82 is designated as "AH22/pAM82".

(iii) The transformed yeast AH22/pTJ102-SOD14 obtained in the procedure (ii) and gained the L-Leucine non-auxotrophism was cultured at 30° C. in 100 ml Burkholder minimal medium [see, Toh-e A. et al. (1973) J. Bacteriol., 113, 727–738] which contained 20 μg/ml L-histidine and 20 μg/ml L-tryptophane. In the logarithmic phase of growth, the cells were harvested and after removal of the medium, 100 ml of a fresh medium was added. The fresh medium contained 20 μg/ml L-histidine and 20 μg/ml L-tryptophane. It also contained $KH_2PO_4$ in an amount one fiftieth that in the Burkholder minimal medium and was instead added with KCl in an amount equivalent to the reduced weight of $KH_2PO_4$. The AH22/pTJ102-SOD14, the culture medium of which had been changed, was cultured at 30° C. for further 24 hours and the resulting cells were harvested. Following the procedure proposed by Goscin et al. Biochemica et Biophysica Acta, 289, 276–283 (1972)], the recombinant h-SOD was extracted and by ion exchange chromatography, the recombinant h-SOD was obtained in its purified form. This procedure will hereinafter be described.

Figure 8:
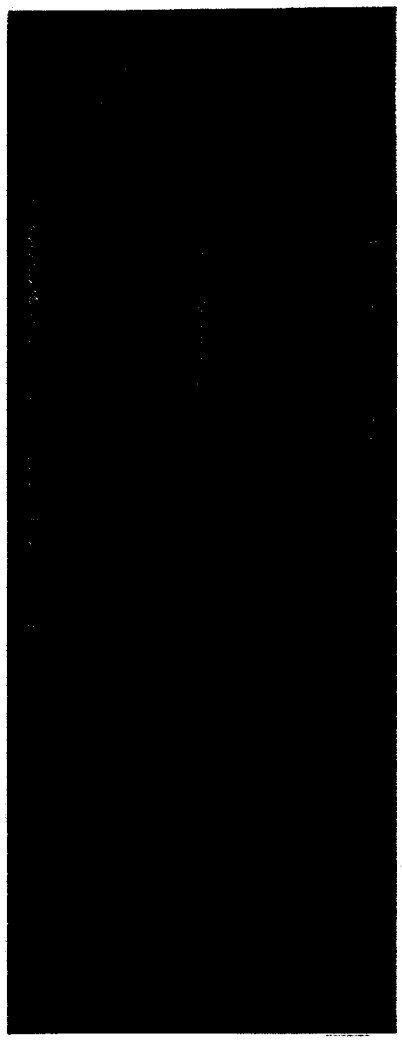
FIG. 8 shows an electropherogram of an h-SOD analogous recombinant polypeptide obtained in Example 5 on the left side and that of the native h-SOD on the right side.

After AH22/pTJ102-SOD14 cells which had been induced for expression by culturing the recombinant h-SOD under the condition of low inorganic phosphate concentration in the above-described manner were harvested and frozen overnight at −20° C., they were thawed at room temperature. A 0.1M $NaHCO_3$ solution was added in an amount of 1.9 ml per gram of wet weight and the resultant mixture was stirred thoroughly to suspend the cells. Furthermore, ethanol-chloroform (5:3 v/v) was added in an amount of 1.1 ml per gram of wet weight and the resultant mixture was shaken overnight at 30° C. By this processing, the recombinant h-SOD was extracted out from the yeast cells. By centrifugation ("RPR 20 Rotor" manufactured by Hitachi, Ltd.; 10000 rpm, 25° C., 10 minutes), the pellet and supernatant were separated from each other and the supernatant was transferred in a separate container. To per ml of the supernatant, 300 mg of $K_2PO_4$ was gradually added in its solid form and was then dissolved. As the container, an Eppendorf tube having a capacity of about 1.5 ml was used. After allowing the solution to stand at room temperature for about 40 minutes, it was subjected to centrifugal separation at 15000 rpm and 4° C. for 1 minutes by a small centrifuge. Of the resulting two layers and the intermediate thin-film like substance, the upper layer was transferred in a separate Eppendorf tube. The container enclosing the upper layer was frozen at −110° C. for 20 minutes, followed by its centrifugation at 15000 rpm and −7° C. for 10 minutes by the small centrifuge. Of the resulting two layers and the intermediate thin-film like substance, the upper layer was transferred in a separate Eppendorf tube. The tube was ice chilled, to which ice-chilled acetone was added in an amount equivalent to 0.75 times the volume of the contents. The resultant mixture was stirred and its ice chilling was continued approximately for further 5 minutes. The container was centrifuged at 15000 rpm and 4° C. for 10 minutes by a small centrifuge and the resulting supernatant was thrown away. The thus-obtained precipitate was dissolved in its entirety in 1 ml distilled water, followed by addition of 1 μl Zn—Cu solution (1M $CuSO_4$, 1 M $ZnSO_4$) and 20 μl potassium phosphate buffer (pH 6.8). In order to remove a precipitate which occurred upon the addition of the Zn—Cu solution, the mixture was centrifuged at 15000 rpm and 4° C. for 1 minute by the small centrifuge. The resulting supernatant was transferred in a separate container. This supernatant was transferred in a "CF25" container (product of Amicon Company; centrifugal ultrafiltration membrane) and centrifuged at 1500 rpm and 4° C. for 10 minutes by using "TS-7 Rotor" (manufactured by Tomy Seiko K.K.). Further, 1 ml distilled water was added to the "CF25" container and centrifugation was conducted again under the same conditions. 300 μl distilled water was again added to the "CF25" container to wash off components which were not allowed to pass through the filtration membrane. The washing was transferred to a separate container. The washing was transferred in a dialysis tube and was then dialyzed overnight at 4° C. against 500 ml 2.5 mM Na-K-phosphate buffer, which had been prepared by mixing 0.5M $KH_2PO_4$ solution and 0.5M $Na_2HPO_4$ solution at pH 6.5 (room temperature) and then diluting the resultant mixture with distilled water. The inner solution of the dialysis tube was taken out and after filtering it through "Column Guard SJHV 004NS" (product of Millipore Corporation), the recombinant h-SOD was fractionated by the method which employed an anionic exchange material. Namely, the recombinant h-SOD contained in the filtrate was adsorbed on a "Mono Q 5/5 column" (HPLC column manufactured by Farmacia AB) which had been equilibrated by the above-mentioned 2.5 mM Na-K-phosphate buffer. After washing off unadsorbed components with the 2.5 mM Na-K-phosphate buffer, the concentration of the Na-K-phosphate buffer was changed linearly from 2.5 mM to 15 mM to elute the recombinant h-SOD from the column. The thus-collected recombinant h-SOD was detected as an active band at the same electrophoretic position as the native h-SOD obtained from human red blood cells (product of Sigma Company) which had been subjected as a control to electrophoresis in accordance with the activity staining method employing an agarose gel film and described in the procedure (v) of Example 1. Results are shown in FIG. 8 (righthand side: the recombinant h-SOD containing Ser at the 111-site of the amino acid sequence and acetylated at the N-terminus thereof; lefthand side: h-SOD obtained from human red blood cells).

In the h-SOD cloning plasmid pTJ102-SOD14, the h-SOD gene is inserted in the downstream of the pho5 promoter derived from pAM82. The transcription of the m-RNA, which contained the h-SOD gene, is effected under the control of pho5 promoter. It has been known that the activities of the pho5 promoter are exhibited, for example, depending on the concentration of inorganic phosphates in a culture medium in the case of the combination of the pho5 promoter and AH22 strain [Miyanohara, A., et al., Proc. Natl. Acad. Sci. U.S.A., 80, 1-5 (1983)]. Accordingly, similar inducible expression is also contemplated in this example. As a matter of fact, the expression control which depended upon the concentration of inorganic phosphates was also observed in the case of AH22/pTJ102-SOD14. The same strains were cultured in the same manner in culture media having different inorganic phosphate concentrations. The cultured cells were subjected to zymolyase treatment and ultrasonic lysing. Thereafter, the amount of h-SOD derivative in the total cell extract from the same volume of each culture was measured by EIA [Enzyme Immunoassay; A specific antibody against Zn- and Cu-type SOD, which had been obtained from human blood, was used.]. Results are summarized in the following table.

| Medium | Strain | |
|---|---|---|
| | AH22/pAM82 | AH22/pTJ102-SOD14 |
| +His, +Trp, +Pi medium | — | 4.2 |
| +His, +Trp, low Pi medium | 3.5 | 295 |

The above values are data obtained by EIA with respect to their corresponding cultured cell brothes of the same volume. The value 3.5 in the table is considered to be the background value. It is also appreciated from the above example that the reduction to the concentration of inorganic phosphate induced the expression of SOD.

Having now fully described the invention, it will be apparent to one of ordinary skill in the art that many changes and modifications can be made thereto without departing from the spirit or scope of the invention as set forth herein.

We claim:

1. A DNA sequence encoding a mutein of human Cu/Zn superoxide dismutase of 153 amino acids, the amino acid at least one of the 6 and 111 position encoded by said DNA being serine or alanine.

2. The DNA of claim 1, wherein said DNA is that of FIG. 1.

UNITED STATES PATENT AND TRADEMARK OFFICE
CERTIFICATE OF CORRECTION

PATENT NO. : 5,239,065
DATED : August 24, 1993
INVENTOR(S) : Hitoshi Sagai, et al It is certified that error appears in the above-indentified patent and that said Letters Patent is hereby corrected as shown below:

On the title page, and Column 1, line 2, in the Title
"CV/2N" should read --CU/ZN--

Signed and Sealed this

Sixteenth Day of May, 1995

Attest:

BRUCE LEHMAN

Attesting Officer        Commissioner of Patents and Trademarks